United States Patent
Zotz

(10) Patent No.: US 8,210,183 B2
(45) Date of Patent: Jul. 3, 2012

(54) DEVICE, SYSTEM, KIT, AND METHOD FOR EPICARDIAL ACCESS

(75) Inventor: Rainer J. Zotz, Herford (DE)

(73) Assignee: Carag AG, Baar (CH)

( * ) Notice: Subject to any disclaimer, the term of this patent is extended or adjusted under 35 U.S.C. 154(b) by 624 days.

(21) Appl. No.: 12/393,253

(22) Filed: Feb. 26, 2009

(65) Prior Publication Data

US 2010/0069820 A1  Mar. 18, 2010

Related U.S. Application Data

(63) Continuation-in-part of application No. PCT/EP2007/059155, filed on Sep. 2, 2007.

(30) Foreign Application Priority Data

Sep. 1, 2006 (EP) .................................. 06119966

(51) Int. Cl.
*A61B 19/00* (2006.01)
(52) U.S. Cl. ....................................................... 128/898
(58) Field of Classification Search ........................ None
See application file for complete search history.

(56) References Cited

U.S. PATENT DOCUMENTS

| 5,452,733 | A | * | 9/1995 | Sterman et al. ................ 128/898 |
| 5,484,425 | A |  | 1/1996 | Fischell et al. |
| 6,126,675 | A |  | 10/2000 | Shchervinsky et al. |
| 6,167,889 | B1 |  | 1/2001 | Benetti |
| 6,332,468 | B1 |  | 12/2001 | Benetti |
| 2002/0092536 | A1 | * | 7/2002 | LaFontaine et al. .......... 128/898 |
| 2003/0033000 | A1 |  | 2/2003 | DiCaprio et al. |
| 2003/0074044 | A1 |  | 4/2003 | Randby et al. |
| 2005/0080439 | A1 |  | 4/2005 | Carson et al. |

FOREIGN PATENT DOCUMENTS

WO  0213703 A1  2/2002

OTHER PUBLICATIONS

VYT Lim, Transradial Access for Coronary Angiography and Angioplasty: A Novel Approach, Singapore Medical Journal, 2003 vol. 44 (11): pp. 563-569.*

* cited by examiner

*Primary Examiner* — Thomas J Sweet
*Assistant Examiner* — Brian Dukert
(74) *Attorney, Agent, or Firm* — Larson & Larson, P.A.; Frank Liebenow; Justin Miller

(57) ABSTRACT

Described are equipment, a system, a kit and a method for the performance of a minimally-intensive body access, such as cardiac access. Epicardial Access Surgery (EAS) is disclosed. EAS does not need general anesthesia or extracorporeal circulation nor does it need a chest opening, which is very advantageous for various aspects. For instance an operation of a coronary artery bypass is created by creating a direct path of flow from one body artery into a coronary artery with the aid of catheter-based minimally-invasive EAS based bypass surgery. In addition, various medical devices are used, such as a special partially flexible needle, a special partially covered stent, and a special partially flexible port.

24 Claims, 13 Drawing Sheets

LAD

DEVICE, SYSTEM, KIT, AND METHOD FOR EPICARDIAL ACCESS

PRIOR APPLICATIONS

This application is a continuation-in-part of International Application No. PCT/EP2007/059155, which in turn bases priority on European Application No. EP 06119966.7.

FIELD OF THE INVENTION

The present invention pertains in general to a method and device for the performance of a cardiac access, such as for bypass treatment of one or more coronary arteries, as well as a system and kit with such devices. In particular, the present invention enables new ways of cardiac diagnostics and therapy, such as a coronary bypass through the creation of a direct path of flow from an aorta into these coronary arteries with the aid of catheter-based minimally-invasive bypass surgery accessed from outside the heart.

BACKGROUND OF THE INVENTION

Coronary heart disease is the most frequent disease of industrialized nations and for more than a hundred years their most frequent cause of death, by far. The community incurs enormous harm through these illnesses, both through the loss of human lives as well as due to the surgical treatment costs of heart patients.

One cause of heart disease is arteriosclerosis of the coronary arteries, which leads to insufficient blood circulation in various areas of the heart musculature. This can lead to heart trouble and a risk of ischemia. In serious cases, an acute occlusion of a coronary artery can lead to irreversible damage of the myocardial tissue, including myocardial infarction and a risk of death.

Previously, a number of solutions for the treatment of coronary artery disease have been developed. In less serious cases, it is frequently sufficient to treat only the symptoms with drugs or the underlying cause of the disease with a change of lifestyle. In the former cases, the coronary occlusion can be treated intravascularly or percutaneously with methods like balloon angioplasty, atherectomy, laser ablation, stents, and suchlike.

However, even these methods of treatment reach their limits and, in general nowadays, a so-called bypass is added if all or the majority of the coronary vessels, are profoundly constricted or are closed and the above-listed alternative methods of treatment fail. In doing so, a connection for the blood stream is created so that a blocked or stenotic or extremely narrow section of a coronary artery is circumvented. More precisely, in a bypass procedure the blood stream to an occluded or blocked target vessel is restored by connecting a source of oxygen-containing or arterial blood with a section of an artery or vein.

In this procedure, the target coronary artery can be any of the coronary arteries arranged around the surface of the myocardium, which supply the heart tissue with blood. Belonging thereto are the right and left coronary artery on the anterior surface of the heart. Often vein segments from the patient's own body serve as the bypass, which were previously removed from the upper and lower leg of the patient. The vein segment is sutured into the coronary arteries distal, or downstream of the bottleneck, with fine sutures, and thereafter directly into the aorta. Alternatively, a rear thoracic wall artery can (i.e. the left arteria mammaria interna (LIMA)) be applied as the bypass. With this blood vessel, the suture is only made distal to the narrowing in the coronary artery. The natural inflow from an anabranch of the aorta is retained, whereas the thoracic wall continues to be supplied by alternative blood vessels thereafter.

The attachment of a blood vessel to another is generally characterized as "anastomosis", for example, the attachment of a graft or a mobilized aorta (e.g. LIMA) to the coronary artery. Normally, the blood vessels are sutured together by the surgeons to create an anastomosis. When using a free graft vessel, an end of the transplant vessel is sutured to an exit artery, such as the aorta, and the other end of the graft is sutured to a target coronary artery, as in the left anterior descending (LAD), which supplies the heart musculature with blood. If a pedunculated or peduncle graft, like the left internal thoracic artery (LIMA), is used for the bypass, the surgeon cuts the LIMA free and attaches the loose end of the LIMA directly to a target coronary artery with sutures. Due to the small proportions (2-5 mm), the stitching of the LIMA to the coronary artery of the heart requires that the treating surgeon is very meticulous. For this purpose, the surgeon uses a magnifying glass with a light source placed on his or her head.

Just a few years ago, bypass operations generally required the opening of the thoracic wall through median sternotomy, the spreading apart of the left and right thoracic wall and the opening of the pericardium, in order to have direct access to the heart. A cardio-pulmonary bypass is normally performed, so that the beating of the heart can be stopped during surgical intervention. This normally requires arterial and venous cannulation, a connection of the bloodstream with a heart-lung machine, cooling of the body to approximately 32° C., aortic cross-clamping, and a cardioplegic perfusion of the coronary arteries to immobilize the heart and cool it down to around approximately 4° C. The complete immobilization or arrest of the heart is generally necessary, as the constant pumping movement of the beating heart would make the operation on the heart difficult at certain times, and at other times, extremely difficult, if not impossible.

When a standstill of the heart has been achieved, the above-mentioned vascular bypass is surgically attached. At the end of the operation, the heart and lungs of the patient are reconnected to their vascular systems, the heart is restarted, and the heart-lung machine is disconnected. Thereafter, the cannula is removed and, finally, the thoracic wall is closed again.

In general, these bypass operations are complex and cost-intensive.

The use of the cardio-pulmonary bypass is often accompanied by difficulties for the patient and increases the costs and the time that is necessary for the procedure. For a cardio-pulmonary bypass, the entire blood of the patient, which normally flows back into the right atrium, is redirected into a system which supplies the blood with oxygen, leads carbon dioxide away, and returns the blood to the aorta of the patient with sufficient pressure for further dissemination into the body. Generally, such a system requires multiple distinct components, including an oxygenator, multiple pumps, a reservoir, a blood temperature regulation system, filters, as well as flow rate, pressure and temperature sensors.

In addition, the contact of the entire blood supply, with which the use of the heart-lung machine is connected, is associated with massive trauma, potential kidney failure, clotting problems, sepsis, heart failure, septal hypokinesia, cerebral perfusion defect, and/or changes in personality, amongst other things, or in the worst case, death.

Furthermore, it can lead to circulatory shock if the heart does not readapt to its original activity after the heart-lung machine is switched off.

In addition, the above-named bypass procedures can not be performed on patients with serious accompanying diseases. Because it is normally necessary to clamp the aorta, deposits are torn free of the vascular wall as embolic material, upon the loosening of the aortic cross-clamp, i.e. the aorta has massive calcifications and scales. An aortic cross-clamp is an instrument for clamping the aorta, so that the heart-lung machine can take over the work completely. If the aorta is calcified in the area of this clamp, plaque can be washed away. As soon as this tissue detritus or other particles have reached the circulation, they can clog other blood vessels and cause an embolism, for which an acute life-threatening complication arises. Embolisms with stroke and perfusion defects in internal organs thus lead to death in a major percentage of bypass patients, even post-operatively after a few days.

Due to the risks that arise during a cardio-pulmonary bypass, man has attempted to perform coronary artery bypass procedures without stopping the heart and without a cardio-pulmonary bypass. Thus many percutaneous and also surgical heart bypass procedures have been developed, which are performed by openings in the intercostal space, as for instance disclosed in U.S. Pat. No. 6,167,889 to Benetti, and U.S. Pat. No. 6,332,468 to Benetti. However, these approaches are still quite invasive.

In addition, bypass and other surgical procedures performed on beating hearts are finding increasingly greater application. However, the need for improved devices continues to exist, which simplify the performance of these procedures and reduce the invasiveness further. The minimally invasive direct coronary bypass (MIDCAB) revascularization with the arteria mammaria (LIMA) to the intraventricular artery (LAD) has established itself in the method as a clinical procedure for a portion of the patients.

For procedures on beating hearts, it depends particularly upon maintaining the hemodynamic function of the heart during the procedure, as required. For example, it has been demonstrated that the manipulation of the heart during a procedure leads to the deterioration of its hemodynamic function, which in some cases can have dramatic, seriously life-threatening consequences for the patient.

In a revascularization (restoration of the blood circulation) on a beating heart by means of a mini-thoracotomy (small thoracic wall opening), the access trauma can be reduced and the use of the heart-lung machine can be done without. However, from a medical point of view, the results are not yet satisfactory, so that the previously named accepted surgical methods can be done without, as a rule.

Recently, the first clinical efforts were made to perform the revascularization of the LAD on a beating heart completely endoscopically and with robotic support. Even in this method, the anastomosis is performed conventionally with surgical suture methodology and, thus, represents a substantial technical challenge which prevents broad application. Even the results of the robotically supported suturing methods are in no way satisfactory from a medical point of view.

Furthermore, it is well known that heart surgeries always become more challenging due to the increasing aging and multimorbidity of the population, and the increasingly scarce working hours of the surgeons. Overall, the entire field is leading to a financially increasing burden on public health.

In Germany alone, for approximately one hundred thousand bypass procedures, several hundred thousand coronary anastomoses are performed by surgeons. The cost for this procedure today equals at least $27,000 per patient. Previously, the procedure is associated with a substantial mortality rate (2-15% depending on patient population, procedure, re-intervention, etc.).

It is therefore preferable to perform a bypass operation without a heart-lung machine with a beating heart, and without involvement of the central blood vessels.

Thus, there is a need for an improved system and method for cardiac access and bypass procedures.

Hence, an improved system and method for cardiac access and vessel access, for instance for facilitating bypass procedures, would be advantageous, and in particular, a system, method or device allowing for increased flexibility, cost-effectiveness, patient comfort, patient safety, and independence of heart-lung machines or minimized invasiveness.

SUMMARY

Accordingly, embodiments of the present invention preferably seek to mitigate, alleviate or eliminate one or more deficiencies, disadvantages or issues in the art, such as the above-identified, singly or in any combination, by providing a system, kit, and method according to the appended patent claims.

The present invention is adapted for an internal method of surgery, diagnosis or therapy through catheterization with a closed thoracic wall without the use of a heart-lung machine, namely Epicardial Access Surgery (EAS). EAS does not require general anesthesia or extracorporeal circulation nor does it need a chest opening, which is very advantageous for various aspects.

According to a first aspect of the invention, a medical device is provided comprising a balloon catheter having an inflatable, expandable balloon centrally arranged at a distal end thereof; a length of a blood tight tubular structure arranged coaxially around said balloon along a defined length at said distal end thereof; at least one expandable fixation unit arranged coaxially between said tubular structure and said balloon; and at least one restriction unit arranged coaxially around said tubular structure.

According to a second aspect of the invention, a system is provided for the performance of a minimally-invasive operation of a coronary artery bypass, characterized by a medical device according to the first aspect of the invention. The system is configured to create a path of flow from one body artery into another body artery with the aid of extracorporeal, regenerative, catheter-based, endoluminal, minimally-invasive bypass surgery, comprising Epicardial Access Surgery (EAS).

According to yet another aspect of the invention, a kit of medical devices is provided allowing performing the method according to the next aspect of the invention. The kit comprises a medical device, according to said first aspect of the invention, and further, a puncture needle, wherein the puncture needle is mounted distal on one end of an endoluminal positionable catheter and is constructed of flexible but hard material.

According to yet another aspect of the invention, a method is provided for the performance of a minimally-intensive surgery of a coronary artery bypass, characterized by creating a flow path from a body artery to a coronary artery with the aid of extracorporeal, catheter-based, endoluminal, minimally-invasive bypass surgery with feedback.

According to still another aspect of the invention, a surgical method is provided comprising puncturing the left antecubital artery and bringing forward a sheath to reach a middle part of the Left Internal Mammary artery (LIMA), advancing a cardiac needle to reach the middle part of the left internal mammary artery, and puncturing the LIMA at said middle part to gain epicardial access.

Some embodiments of the invention provide for a seminoninvasive medical procedure or enablement thereof.

Some embodiments of the invention provide for a medical procedure may be performed in a very fast manner as compared to intra thoratically. For instance, cardiac bypass procedures are feasible to be performed in approximately 10 to 60 minutes depending on the number of bypass vessels.

Some embodiments of the invention provide for a medical procedure may be performed in patients who were not accepted for conventional bypass before.

Some embodiments of the invention provide for a medical cardiac bypass procedure which may be performed in a number of diagnoses excluding conventional bypass, such as renal insufficiency, peripheral arterial occlusive disease, progressive heart failure, or any serious comorbidity.

Some embodiments of the invention provide for a medical procedure may be performed in a catheterization laboratory as a routine procedure.

Some embodiments of the invention provide for a medical procedure may be performed in a catheterization laboratory as a bail-out procedure when a conventional percutaneous endoluminal intervention has failed or led to a complication and the patient is in danger of losing his or her life.

Some embodiments of the invention provide for a medical procedure may be performed in very sick hearts.

Some embodiments of the invention provide for almost no or very little blood leakage, whereby a previously necessary blood supply and related blood donation procedures and risks are avoided.

Some embodiments of the invention provide for a medical procedure may be performed without central anesthesia.

Some embodiments of the invention provide for a medical procedure may be performed without a heart-lung machine.

Some embodiments of the invention provide for a medical procedure may be performed without blood products and circulatory support, as in catecholamines or any other drug supporting heart surgery or anesthesia.

Some embodiments of the invention provide for a medical procedure which is suitable for the use of autologous material, which minimizes immunological or rejection complications.

Some embodiments of the invention provide for a medical procedure may be performed via the LIMA or RIMA or any non-central vessel in the neighborhood of the A. axillaris (arteria axillaris).

Some embodiments of the invention provide for a medical procedure may be performed via the Aorta with the help of an occlusion balloon, such as a Heart Port Access™.

Some embodiments of the invention provide for a medical procedure may be performed semi-invasively from arteries of the stomach, as in the *A. gastroepiploica*.

Some embodiments of the invention provide for a medical procedure may provide a bypass of leg arteries or arteries in the neck or any other region of the human body.

Further embodiments of the invention are defined in the claims, wherein features for the second and subsequent aspects of the invention may be altered without departing from the scope and spirit of the invention.

It should be emphasized that the term "comprises or comprising" when used in this specification, is taken to specify the presence of stated features, integers, steps or components, but does not preclude the presence or addition of one or more other features, integers, steps, components or groups thereof.

BRIEF DESCRIPTION OF THE DRAWINGS

These and other aspects, features and advantages of the invention will be apparent and elucidated from the following description of embodiments of the present invention, reference being made to the accompanying drawings thereof, in which.

DETAILED DESCRIPTION

Figure 1A:
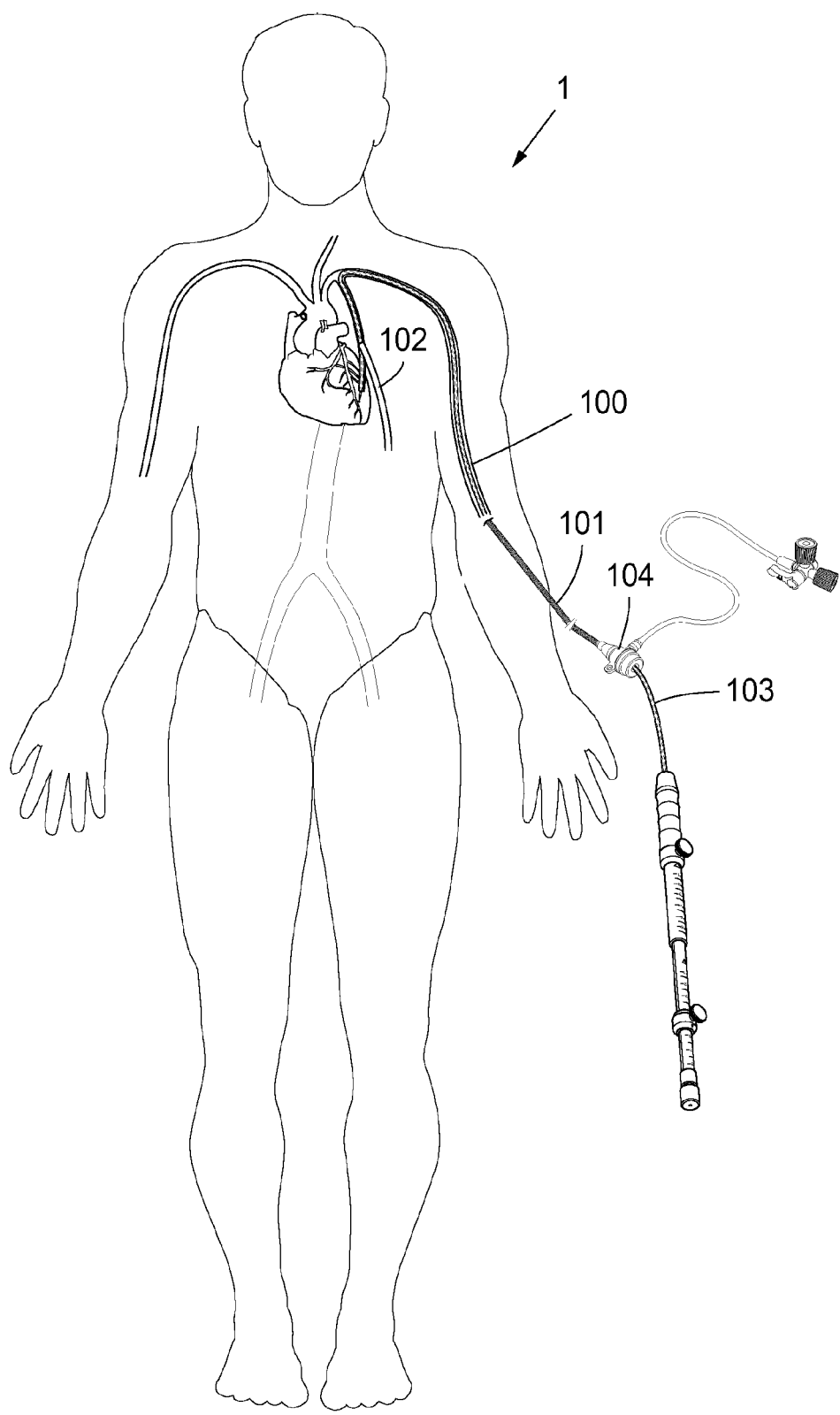
FIG. 1A is a schematic overview of the principal path of access and method of a minimally-intensive epicardial access. (for instance useful for a bypass operation where the left arteria mammaria (LIMA) is internally anastomosized to the coronary artery (LAD or other blood vessel)

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to a medical cardiac bypass procedure. However, it will be appreciated that the invention is not limited to this application but may be applied to many other cardiac diagnostic, therapeutic, and surgical procedures including, for example, epicardial electrophysiology.

Alternatively, this procedure may be applied to any bypass situation in the human body, such as the leg (arterial bypasses for peripheral occlusive disease) or the carotid artery in the neck.

In addition to the internal mammary artery (LIMA), a bifurcation may be built artificially from the right or left axillary or subclavian artery in which the vessel is directly punctured endoscopically with a needle and an instrument is brought forward, as described below for the LIMA.

While the invention is described in different embodiments and with the description of various surgical methods for the making of the invention, the skilled person understands that these embodiments represent only illustrative, non-limiting examples of various forms, which the present invention may take.

More precisely, some of the described embodiments of the equipment and the system of the present invention are adapted for the carrying out of a minimally-intensive surgical cardiac bypass procedure. The method is characterized by percutaneous access, which is performed using peripheral catheterization. Due to the endoluminal method used, the heart can beat normally during the procedure and does not need to be slowed or completely arrested.

An example for such a method for the performance of a coronary bypass operation will be described in detail further below.

Firstly, the novel access way to the cardiac region is elucidated.

As illustrated in FIG. 1, after puncturing the left antecubital artery 100 a catheter having a sheath 101 is brought forward to reach the middle part of the left internal mammary artery (LIMA) 102. By way of the sheath 101, a special cardiac needle 103 is advanced to reach the middle part of the left internal mammary artery 102.

An introducer sheath suitable for this purpose is described in U.S. Pat. No. 5,484,425 to Fischell, et al., which is incorporated herein by reference in its entirety.

Figure 2:
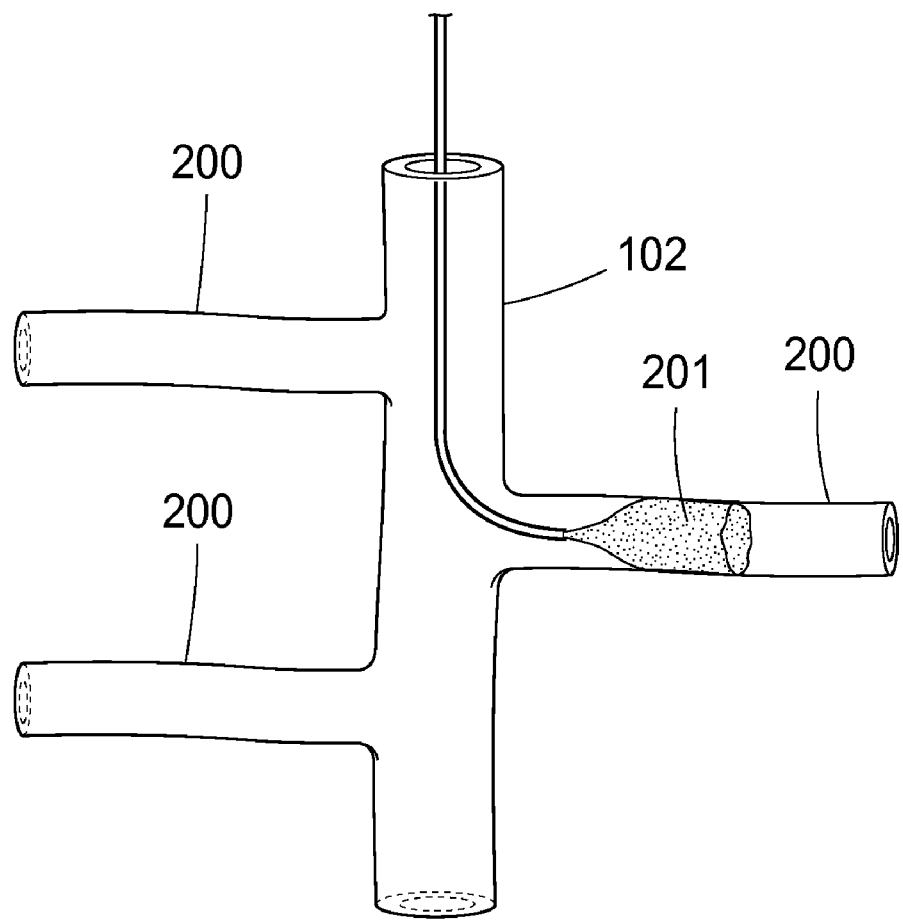
FIG. 2 is an illustration of how a catheter is used to close side branches.

The catheter side branches 200 of the artery 102 are reached and occluded with small amounts of collagen or thrombin or other substances 201, as illustrated in FIG. 2. Also the very distal part of the LIMA can be occluded with such a procedure.

Alternatively or in addition, catheter delivered collapsible occlusion devices may be used to occlude the vessels in a suitable manner. Medical devices for such vessel occlusions are, for instance, described in European patent EP 0808138A, of AGA Medical Corp., which is incorporated herein by reference in its entirety.

The Internal Mammary Artery (IMA) is a blood vessel located on the inside of the chest cavity. It is an artery, not a vein. Therefore, it carries oxygenated blood under the same blood pressure as that seen in the aorta or the coronary arteries themselves. There is one IMA on each side of the sternum. This unique blood vessel runs along the inside edge of the sternum, sending off small branches to the bones, cartilage, and soft tissues of the chest wall. These side branches may be occluded as mentioned above. For unclear reasons, the IMA is remarkably resistant to cholesterol buildup and only very rarely atherosclerosis is seen in the IMA vessels. This makes it well suited for a bypass graft vessel.

The IMA is also conveniently located near the most important coronary branch, the left anterior descending (LAD). In open heart surgery, a surgeon can transfer the lower end of the IMA down to the heart surface to use as a bypass graft to the coronary vessels, as described below. As compared to veins from the lower extremity, the IMA is smaller and more delicate. However, the use of the left internal mammary artery (LIMA) is associated with improved long term results from coronary artery bypass surgery.

Sometimes the LIMA is too small to use. And in other cases, the vessel is so delicate that just the steps taken to remove if from underneath the ribs will cause harm to the vessel wall, making the IMA useless. However, in a large percentage of open heart coronary bypass operations, this vessel is the best conduit available for surgical bypass to the major arteries of the heart.

Alternatively, the greater saphenous vein (GSV) from the lower extremity may be utilized as an autograft. The GSV is quick and easy to harvest, long enough for bypass vessels, has strong tissue, is not as delicate at the IMA, is larger in caliber than the IMA, making surgery technically easier. However, LIMA grafting patients enjoyed better long-term results when compared with patients receiving only vein grafts.

Figure 16A:
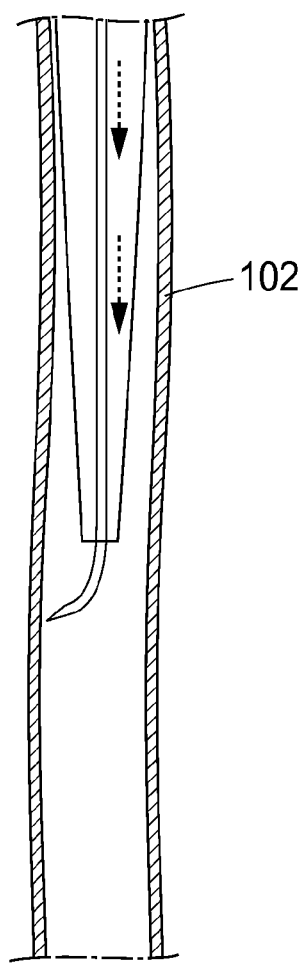
FIGS. 16A and 16B are illustrations of a cannulization of the LIMA sideways with a needle and connection to the LAD.
Figure 16B:
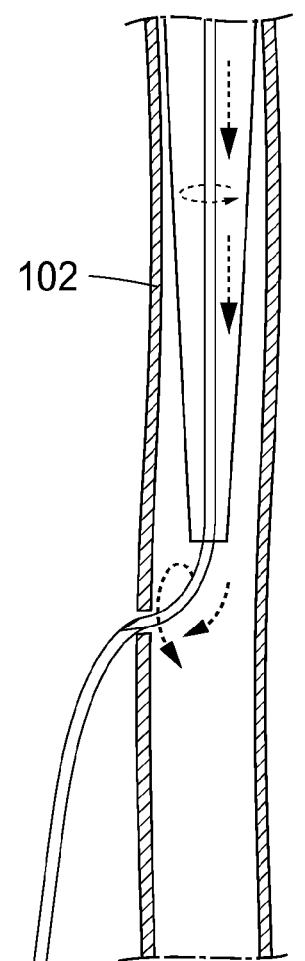

As illustrated in FIG. 16A, with the aid of fluoroscopy and a stiff introducer bended at its tip, the needle tip is bended dorsally in order to leave the vessel. The needle is then retracted into the needle sheath. The latter is steered to the direction of the distal part of the left anterior descending coronary artery (LAD). In several fluoroscopic projections, the correct position is defined. Then the puncture of the healthy distal LAD is performed, which is a delicate maneuver. This is achieved by a very fast advancement of the needle in its sheath from an angle of about 45°. After the correct puncturing of the distal LAD has been assured by pressure measurement and contrast injection, a conventional guide wire is advanced into the distal LAD preferentially until it ends.

Figure 3:
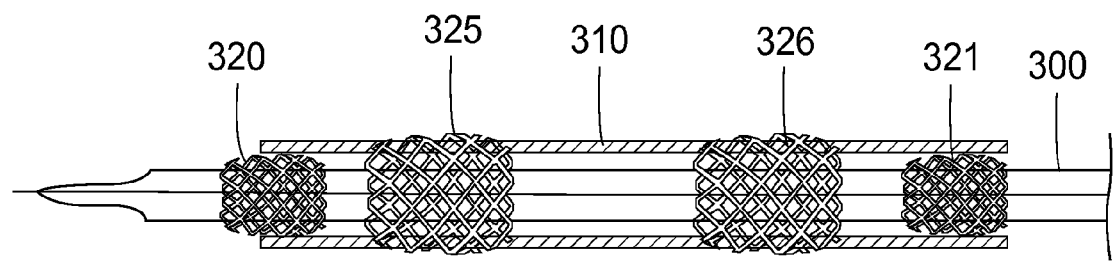
FIG. 3 is an illustration of a catheter balloon assembly comprising a graft vessel outwardly constrained onto a balloon and inwardly comprising expandable fixation units for anastomosing the vessel on place in the body.

By way of this guide wire, a conventional long balloon catheter is advanced to the LAD puncturing site after the needle and its protection sheath has been retracted. The long balloon catheter (approximately 10 cm in length for an adult patient) is advanced in order to widen the puncturing site in the LAD. At the more proximal parts, this balloon catheter is armored with a vein (GSV) or artery (LIMA) which had been explanted before using a standardized procedure. Alternatively or in addition, an artificial vessel graft may be loaded to the balloon catheter. Such an assembly is illustrated in FIG. 3, where an autologous or artificial vessel 310 is assembled on a balloon catheter. In case of an autologous vein or artery, this may have been harvested endoscopically. The vessel 310 may such be transported to a site of implantation, such as the heart, and later anastomosed.

As can be seen in FIG. 3, two conventional first stents 320, 321 have been crimped to the proximal and distal end of a conventional balloon 300, resulting in a first assembly.

On this first assembly, the artificial or autologous vessel 310, for instance a vein, or artery, has been placed. The vessel 310 is fixed to the first assembly with two further conventional stents 325, 326 by crimping them more centrally so that the vessel 310 is fixed securely to the balloon 300. This fixation is arranged such that it holds for transport to the location of anastomosis. In this manner, an assembly is provided as illustrated in FIG. 3.

In the assembly, the two stents 320, 321 are arranged on the inside of vessel 310 at the ends thereof as inner stents, and the two other stents 325, 326 are arranged in-between as outer stents. The stents 325, 326 arranged on the outside of the vessel 310 are arranged to hold the vessel on the balloon 300, at least during delivery.

The stents 325, 326 arranged on the outside of the vessel 310 may be made of a biodegradable or bioresorbable material. In addition or alternatively to stents other fixation units may be used, such a strands of elastic material, in some embodiments biodegradable or bioresorbable. At least one fixation unit is comprised in the assembly for holding the vessel 310 on the balloon 300.

As illustrated in FIG. 3, the artery or vein has been fixed onto the balloon 300 catheter using two external crimped stents 325, 326. In addition, one further stent is crimped underneath the artery or vein at the proximal and distal border of the balloon 300 reaching beyond the proximal and distal end of the artery or vein.

Figure 3A:
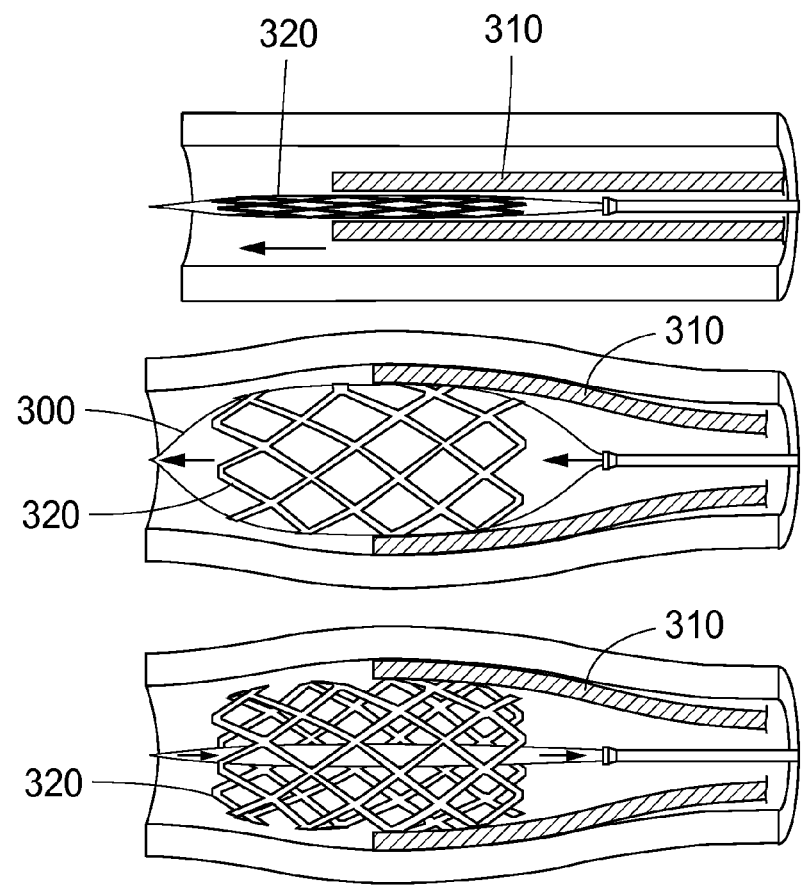
FIG. 3A is an illustration of the catheter balloon assembly according to FIG. 3 in use.

As illustrated in FIG. 3A, after correct placement the balloon 300 is inflated. The latter stents will loose their function and just stay in place and serve as a location marker later on, or may be degraded or resorbed after implantation.

The stents 320, 321 crimped first will serve as junction to the proximal and distal anastomosis because they overlap to the vessels to be anastomosed, such as illustrated with the stent 320 to the left in FIGS. 3 and 3A. They are in one part in the vessel to be anastomosed and in the other part in the artery or vein being anastomosed. Alternatively or in addition, these "inner" stents arranged inside the vessel 310, may be arranged at an end portion of the vessel 300, as illustrated with the stent 321 to the right in FIG. 3, which provides a sufficient fixation of vessel 310 at the site of anastomosis. The stents and the balloon may have location markers. The native coronary vessels and the bypass artery or vein can overlap in order to ensure tightness of the anastomosis. The "inner" stents 320, 321 may be of a metal, such as a shape memory alloy, for instance Nitinol. In addition, the inner stent may be a covered stent in order to improve tightness of the anastomosis.

Alternatively to having two inner stents, one at each end of the vessel 310, a single longer stent may be provided on the balloon 300, extending continuously between the two ends of the vessel 310.

The assembly may also comprise an artificial prosthesis, such as a GoreTex graft, and the procedure may be performed with the artificial prostheses in analogy.

Figure 4A:
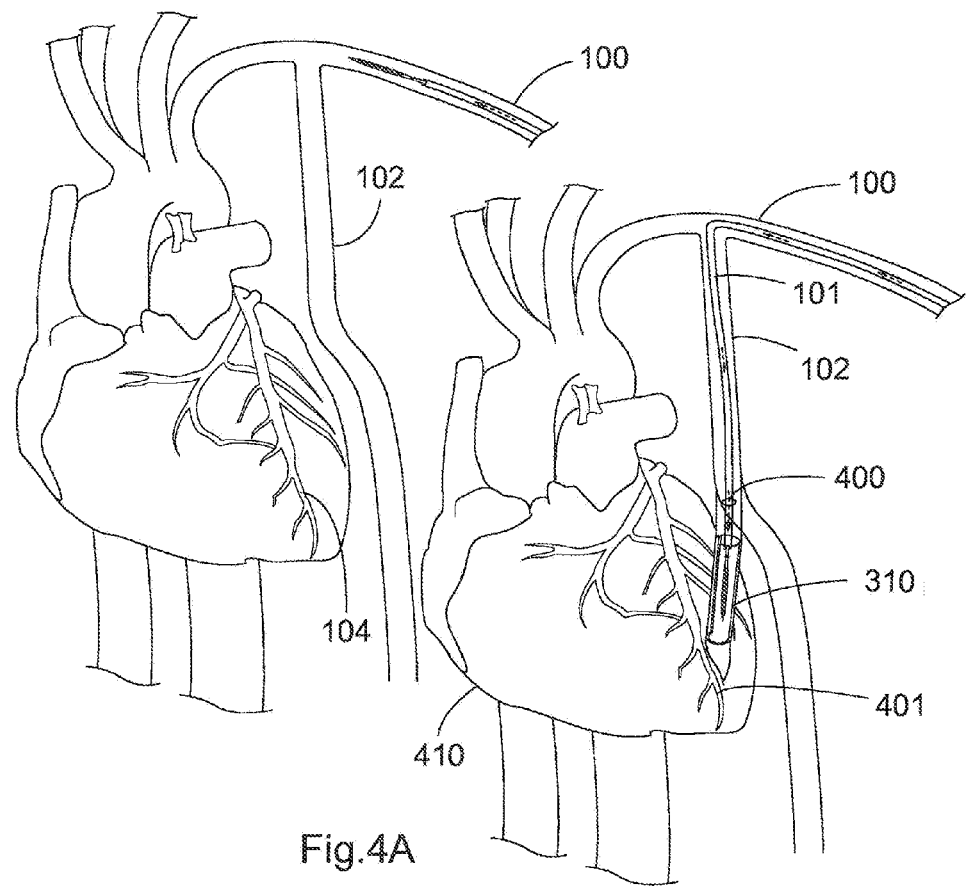
FIG. 4A is an illustration of a catheter based LIMA-LAD bypass, on the right with a catheter balloon assembly according to FIG. 3.
Figure 4C:
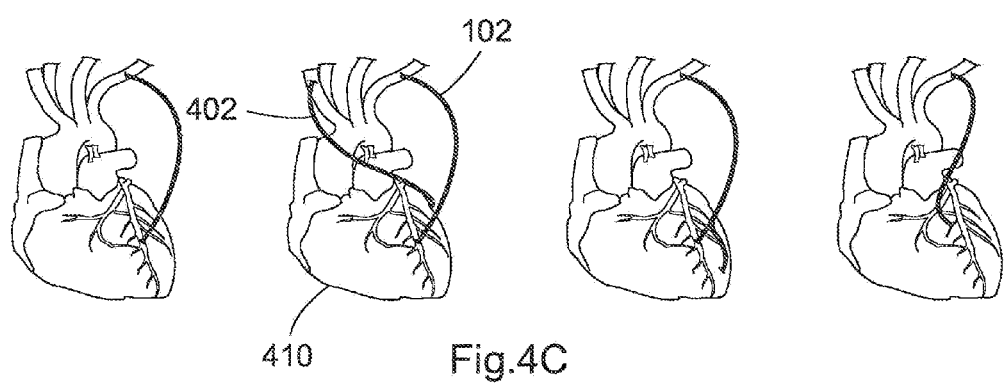
FIG. 4C is illustrations of further LIMA and RIMA (right arteria mammaria interna) bypasses.

Referring to FIGS. 3A and 4A, the anastomosis is now performed in that the distal stent 320 underneath the balloon 300 is brought into the LAD 104, and the proximal stent 321 is partly left within the LIMA 102. Thus, with inflating the balloon 300 the proximal stent 321 produces a connection between the LIMA 102 and the implanted artery or vein 310, and the distal stent 320 creates an anastomosis with the artery or vein 320 and the LAD 104. Thus, a bypass between the LIMA 102 and the LAD 104 has been created. Blood will flow as soon as the sheath 101 has been removed from the LIMA 102.

With regard to a distance measurement, this is not critical in the present procedure. It is not necessary to exactly match the length of the vessel 310 with the distance between the LIMA puncturing site 400 and the LAD puncturing site 401 as long as the vessel 310 is longer than this distance, since any excess length of vessel 310 will just fit in the space between the lung and heart 410. Measurement may be performed with radio-opaque fiducial markers on the guide wire.

Any blood leaking out of the LAD 104 or the LIMA 102 may be punctured as a pleural or pericardial effusion, as is the case with conventional surgery. However, with this procedure and its possibility to create anastomoses very fast, much smaller amounts of blood leakage occur.

Instead of the LIMA, the right internal thoracic coronary artery (RIMA) 402 may also be used as an access way.

Figure 1B:
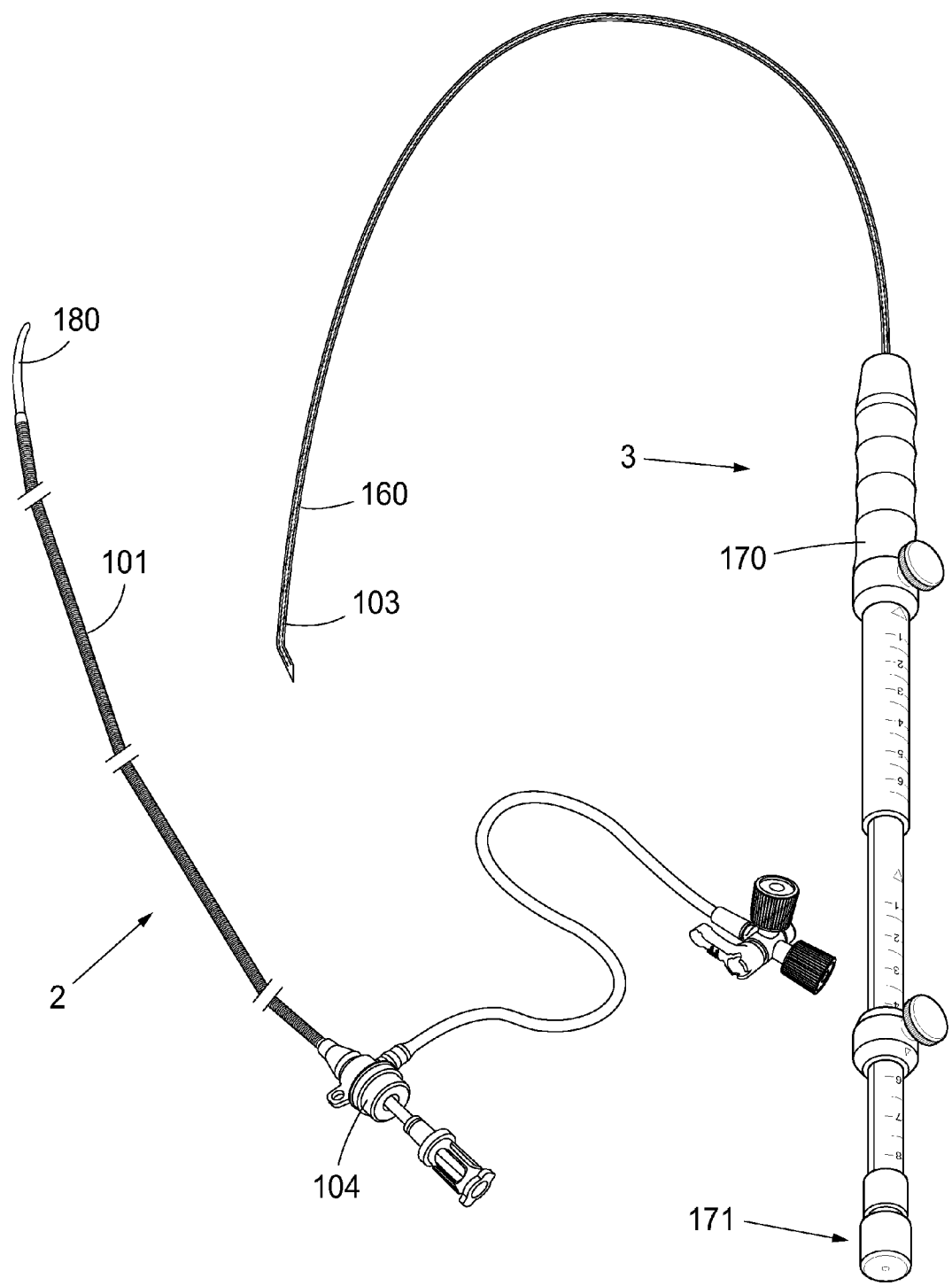
FIG. 1B is an illustration of a catheter port and a needle for EAS.

Puncturing is performed using a puncturing device, such as the needle 103, shown in FIG. 1B. The puncturing device may be of the type shown in WO 2004/028613, which is incorporated herein by reference in its entirety.

If necessary, the LIMA may be punctured again proximally, and the newly implanted vessel may also be punctured and a further vessel implanted using the same mechanism. Therefore, a full arterial or venous revascularization may be achieved, in analogy to conventional open heart bypass surgery that is using extracorporeal circulation.

This procedure may use genuine autologous body material (arteries and veins) and conventional bare metal stents in order to fix arteries and veins into their place. Other material like drug eluting stents and artificial blood vessels may be used as well as stents 320, 321.

The venous access in the internal thoracic vein can also be used as an access route, and as an access to treat complications.

This anatomical access way that is provided by the present method, other devices, tools and/or assemblies, may be brought forward to the epicardium, the innermost layer of the pericardium, which is the membranous sac enclosing the heart. For instance, instruments like imaging instruments, such as catheter based nuclear, ultrasound (US), magnetic resonance (MR) or thermographic scanners may be advanced to the epicardium. In this manner, a diagnosis is provideable before or during a cardiac therapy or surgical procedure.

Before performing therapeutic intervention, as in the described internal bypass, a diagnostic procedure may be performed in order to make a more correct diagnosis. For this purpose, a thermography catheter, an ultrasound probe, an MRT coil, or an electrophysiological catheter may be introduced via the LIMA into the epicardial space, for instance, introduced through sheath 101, in order to assess epicardial pathways and electrical currents.

High resolution ultrasound probes may be used to evaluate cardiac performance and perfusion at accuracy which had not been possible before.

High energy ultrasound probes may be used to provide therapeutic procedures from the epicardial direction, introduced through sheath 101 as described above. In this manner, for instance, calcifications existing in the cardiac vessel system may be destructed by directed ultrasound energy. Due to the precise positioning adjacent a site of calcification, this may be performed with less energy than previously necessary, and is more patient friendly since side effects may be prevented.

An electrophysiological catheter may also be used to ablate epicardial electrical pathways from the epicardial space, which were not amenable before.

Figure 5:
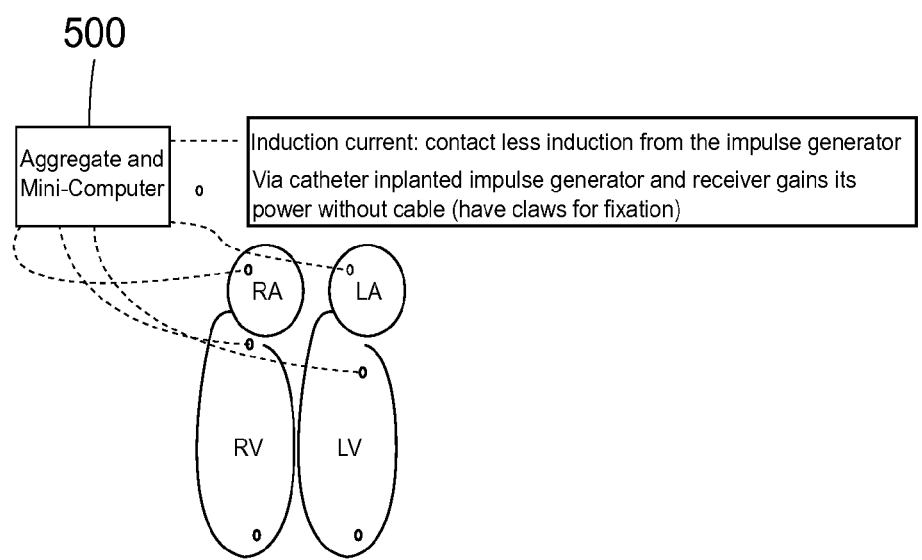
FIG. 5 is a schematic diagram of an epicardial cardiac impulse generator.

The epicardial access may also be used to implant miniaturized electrodes for functioning of an epicardial pacemaker 500, as illustrated in FIG. 5.

In order to provide a visualization of the procedure, an endoscope may be used. The endoscope may be introduced intercostally into the thorax. Less invasive is to use an endoscopic device of small diameter fitting into a vessel. The endoscopic catheter may have a steerable tip by means of which the access passage in the thorax may be determined optically.

Electrophysiological examinations are provideable epicardially. Moreover, an implantation of pacemakers or similar devices is provideable epicardially. These methods and systems are elucidated in more detail below.

Therefore, a series of previously impracticable diagnostic, surgical, and/or therapeutic devices and procedures is opened up through free, uncomplicated access to the outer heart wall (epicardium), which is made possible through the above-described instruments and methods. For example, completely new possibilities within the framework of so-called electrophysiology are opened up. Electrophysiology is a special field for the investigation of cardiac depolarization and treatment of heart rhythm disturbances within internal medicine or cardiology. Previously, multiple thin electrode catheters were inserted into the right heart by means of the groin veins using X-ray fluoroscopy after local anesthetization. In this process, the electrode catheters measure intracardiac, such as the electrical depolarization in the interior of the heart, in order to determine the mechanism of the heart rhythm disturbances. The electrical signals at various locations of the heart are recorded by means of the electrode catheters and the heart rhythm disturbances are triggered with the aid of pacemaker impulses that cannot be felt by the patient, whereby a diagnosis of the heart rhythm disturbance may be made.

Now an electrophysiological diagnosis and therapy with special electrical catheters from outside the heart in the thoracic cavity is made possible with the aid of the devices and access methods described herein. As described above, an electrophysiological diagnosis and therapy previously occurred only from endocardial, as in from inside the heart out. Consequently, new possibilities for cardiac diagnosis and therapy are opening up through the peripheral minimally-invasive access path to the pericardium and the possibility to be able to epicardially get to all locations of the pericardium.

The data acquired through such pericardial electrode catheters may be used for three-dimensional (3D) mapping. In addition, these 3D data may also be combined with imaging datasets, for example in CT systems, in order to furnish cardiological images.

Furthermore, electrodes may be inserted into the heart through an access path described herein, which are suitable for measuring both electrical cardiac signals, as well as for the delivery of electrical energy for the introduction of impulses into the heart tissue and the triggering of depolarization. For example, minimally large electrodes may be inserted 1-2 mm into the heart tissue to remain there.

The energy necessary for the impulse current is preferably transmitted wirelessly to such implanted electrodes, for example through induction. The electrodes optionally have an energy storage unit, such as in a capacitor with high storage density (Supercap), which stores rectified, wirelessly transmitted energy and provides energy for impulses. The energy may also be used for the supply of the remaining electronics of the electrode, such as for wireless data transmission.

The energy that is fed into the electrodes may originate from various sources, such as a device like a conventional pacemaker implanted under the skin of the patient with a built-in or rechargeable independent energy source. This device may be significantly larger than the wireless electrodes and consequently stores substantially more energy. In this process, the so-called "leads", cables to the electrodes, are not required and the conventional problems associated therein are avoided, such as a cable breakage. In the alternative, the energy may also originate from a device worn on the outside of the body, or transmitted by means of a catheter, such as through ultrasound energy.

The above-mentioned device implanted under the skin comprises an assembly for the mentioned energy transmission, for example, a wireless two-way communication device for communication with the electrodes and a mini-computer for regulation.

The wireless electrodes have means for fastening to the cardiac muscle (myocardium), such as claws for adherence in the myocardium. Preferably, the wireless electrodes are kept very small so as not to unnecessarily burden the beating mass of the myocardium through inertia force.

Any number of wireless electrodes may be implanted through the catheter. In such a manner, a physiological model of depolarization and repolarization may be simulated. However, whereas a significantly lower risk of infection exists than previously, as less material is used, no cable leading to the electrodes is necessary. Because the electrodes are mounted on the exterior of the myocardium, no risk of thrombosis exists, as well.

By means of suitable implanted wireless electrodes, for example six electrodes, the coordination of all four heart chambers is possible with one electrode outside each of the atria (right atrium RA, lift atrium LA), one electrode each on the exterior myocardium in the area of the transition to the right and left ventricle, and one electrode outside of each of the ventricles (right ventricle RV, left ventricle LV).

Additional pulse generators are feasible for patient-required particularities. A main advantage is that a physiological depolarization and repolarization may be provided analogous to the physiological conductive system of the heart. Conventional electrodes still rely on the function of the natural conductive system. The wireless electrodes or pulse generator may purposely be implanted where the conductive system is interrupted. The pulse generators are mounted precisely ("shot") where current and excitation conduction is lacking. Localizations are achieved that are not achieved with remote-controlled cables.

Thoraxscopy may be advantageously performed by means of Epicardial Access Surgery (EAS). In this manner, the external evaluation of the complete lung, internal mediastinum and pleural space on both sides of the body may be performed advantageously.

Figure 4B:
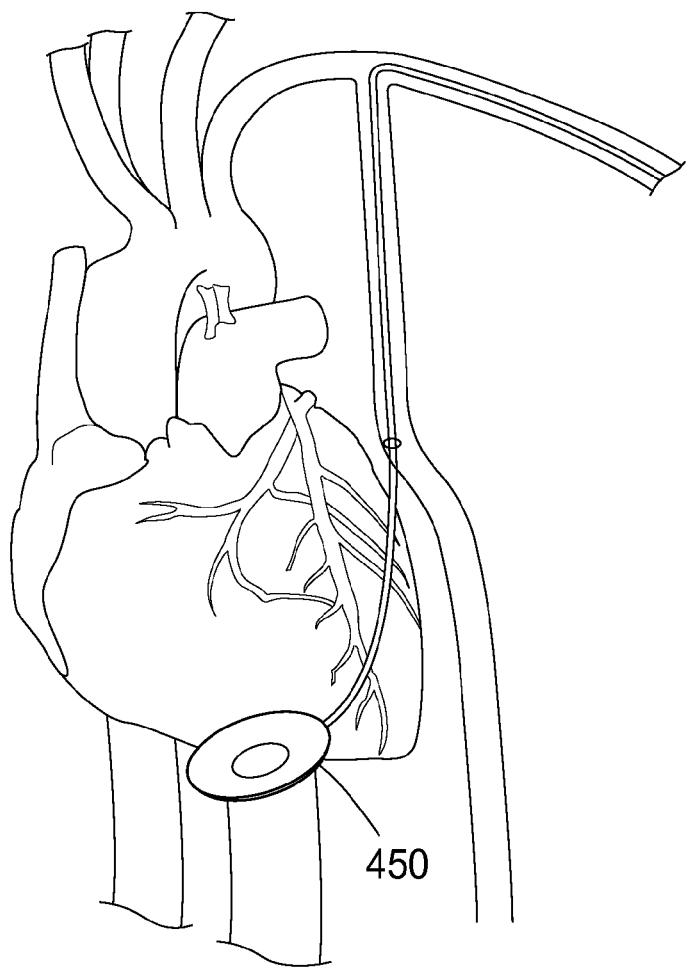
FIG. 4B is an illustration of a catheter based leverage device for manipulating the position of the heart.

As illustrated in FIG. 4B, a tool 450 like a spoon, may be used to lift the heart a shorter distance in order to reach rear sections. The access is then professionally closed, for instance with a reverse Angio-Seal system or with a Starclose™ system. Also, other bioresorbable devices for sealing punctures may be used, such as described in U.S. Pat. No. 6,126,675 to Shchervinsky, et al., which is incorporated herein by reference in its entirety. In these cases, collagen or a closure device is applied from outside the body onto the vessel to be closed at the puncture site in the body. Thus, there is no risk of internal thrombosis complications. Alternatively or in addition, a covered stent may be used to close the vessel at the puncture site. Therefore, a closure of the A Mammaria may be achieved with an inverse Angio-Seal™, or a Starclose™, or a covered stent.

The Angio-Seal™ Vascular Closure Device of St. Jude Medical is originally designed to quickly seal femoral artery punctures following catheterization procedures, allowing for early ambulation and hospital discharge. The device creates a mechanical seal by sandwiching the arteriotomy between a bio-absorbable anchor and a collagen sponge, which dissolves within 60 to 90 days. By using the Angio-Seal™ inversely, the vessel at the internal puncture site in the body may be reliably closed when finalizing Epicardial Access Surgery (EAS). The Angio-Seal™ is used and applied in a novel way, providing a uniform and secure seal of the internal puncture site.

The StarClose™ Vascular Closure System (VCS) of Abbott Medical Systems is also conventionally used to close a puncture site in the femoral artery and stop bleeding following a diagnostic cardiac catheterization procedure. After a cardiac catheterization procedure it is necessary to stop the bleeding in a blood vessel in the leg (the femoral artery). The StarClose™ VCS uses a nitinol clip to stop bleeding by closing the hole in the artery. The catheter is removed and the StarClose™ VCS is conventionally used to clip the hole in the femoral artery closed. By using the StarClose™ Vascular Closure System (VCS) internally, the vessel at the internal puncture site in the body may be reliably closed when finalizing Epicardial Access Surgery (EAS). The StarClose™ Vascular Closure System (VCS) is used and applied in a novel way providing a uniform and secure seal of the internal puncture site.

As mentioned above, a bypass operation without a heart-lung machine with a beating heart without involvement of the central blood vessels is now provided and may be performed in an advantageous way.

However, the fact that a completely percutaneous operation may be performed does not exclude the combination with partially known procedure segments.

The method is effected endoluminally from inside a blood vessel out to a vessel to be bypassed, such as a coronary vessel. In addition, a blood vessel to be used for a bypass may be detached from the inside out. This may, for instance, happen mechanically or by cauterizing the environment, for example through a lever. Even a non-contact detachment from the wall is feasible with the help of high-level ultrasound from a catheter, delivered as described above.

EAS is now described in more detail with reference to a cardiac bypass surgery based on EAS.

Figure 6:
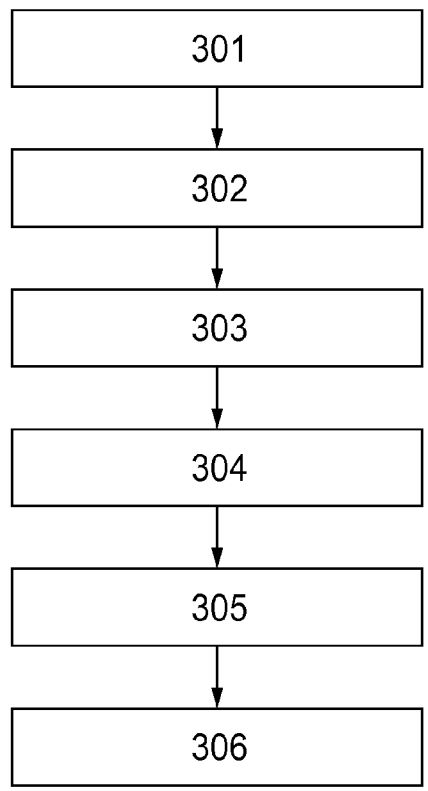
FIG. 6 is a schematic diagram of the steps of a method of an EAS bypass operation in accordance with FIG. 1A.

The method described as an example in accordance with an embodiment basically comprises the following parts, as shown in the schematic diagram of FIG. 6.

First of all, the percutaneous probe of the left arteria mammaria interna (LIMA) takes place from the left arm or from the left shoulder. The probe of the LIMA occurs with a flexible port, whose movement is controllable from the arm out. The port is sealed up proximally (step 301 of FIG. 6).

Secondly, the mobilization of the LIMA occurs with a catheter-based instrument (step 302 of FIG. 6).

Thirdly, the occlusion of the side branches occurs, for example with collagen, thrombin, or alcohol (step 303 of FIG. 6).

Fourth, the relocation of the distal LIMA occurs, for example with the help of cryoablation or radio frequency (RF) ablation (step 304 of FIG. 6).

Fifth, the probe of the LIMA occurs, for example with a fine Brockenborough, and the distal LAD is cannulized with a needle (step 305 of FIG. 6).

Lastly, a wire is inserted and the vessels are connected with the help of an anastomosis, with a proximal covered stent or alternatively with a mobile distal stent portion, which enables the flow proximally, whereas the proximal stent portion is coated with drugs, if necessary (step 306 of FIG. 6).

This endoluminal therapy of coronary vessel blockages is a fully-fledged alternative to conventional surgical therapy. The patient can thereby be offered such a procedure, and for this purpose an interdisciplinary surgical-radiological coordinated proceeding is necessary, as well as high-level expertise and regular practice in the application of endoluminal stent implants and an available supply of stent implants of various sizes. The requirements are fulfilled in each heart catheter laboratory.

Hereinafter, the methods illustrated in FIGS. 1 and 6 are described in detail with the help of which the left arteria mammaria interna is anastomosized to a coronary artery.

I. Percutaneous Cannulization—Step 301:

The patient 1 (shown in FIG. 1), on whom the operation is being performed, can be prepared in a conventional manner for a cardiac bypass operation. The preparation of the patient, the anesthesia used and the path of access to the coronary circulation can vary. However, they are generally similar to the preparation of a coronary angiograph procedure.

The patient may be brought into general anesthesia. For example, standard cardiac or operative anesthetic techniques can be used, just like the premedication with Diazepam, induction with Propofol and Sufentanyl, and maintaining of anesthesia with Desfluran. In doing so, artificial ventilation and monitoring of the vital parameters of the patient is necessary.

However, local anesthesia of the cannulization location can suffice without artificial respiration.

Following the preparation, access to the coronary artery vascular system of the patient is attained from the selected route of approach. In the present example, a percutaneous punction to the left arm on the left shoulder is made for the purpose of probing the left arteria mammaria interna (LIMA).

First, a catheter 101 is inserted into the vascular system by means of an incision in the left arm or on the left shoulder and moved forwards. Because this sequence does not allow any direct visualization of the coronary vascular system, as with an open thoracic wall or by using an endoscope introduced intercostally, a picture-producing modality may be used, as in an angiography X-ray unit, which is standardly used for the localization of coronary diseases, PTCA (Percutaneous Transluminal Coronary Angioplasty) procedures or stent placement. Because the access is gained through a catheter, which is applied from outside, the customary tissue injury is minimized.

A pneumocardial bypass is unnecessary. However, the method is in no way restricted in the event that a pneumocardial bypass would be performed. Therefore, a heart-lung machine may be kept ready for critical patients.

It is to be anticipated that sicker patients are to be expected for NICAB (non-invasive coronary artery bypass grafting) or PCB (percutaneous coronary artery bypass grafting), as the method is inherently more gentle. If desired, the heart may be slowed while the coronary vascular system is catheterized. Such slowing can improve the visualization of the catheter. Standard pharmacological methods to slow the heart are well-established in the literature.

The catheter is moved within the vascular tree through continual forward movement to the target location in the left arteria mammaria interna (LIMA). This is enabled, in that the catheter tip is controllable. The position is monitored with the aid of imaging equipment.

II. Mobilization of the LIMA—Step 302:

When the distal end of the access catheter is positioned in the LIMA, the mobilization of the LIMA takes place in step 302 with a catheter-based instrument. The mobilization of the distal LIMA was previously not feasible, as this was seen as technically difficult. However, the mobilization of the LIMA is attained in the following manner.

Figure 7A:
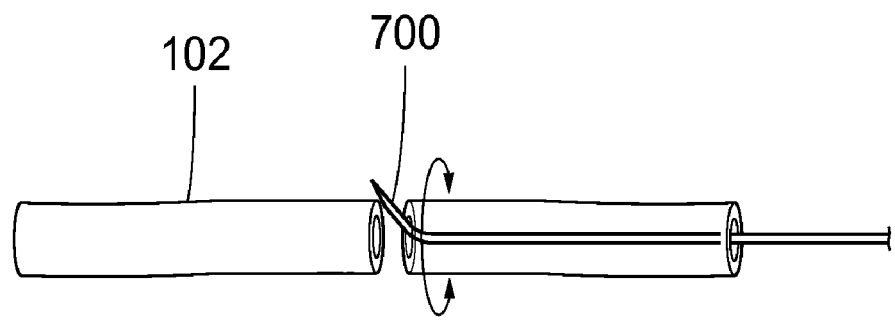
FIGS. 7A, 7B and 7C are illustrations of various tools and methods of detachment of a blood vessel, such as the distal LIMA arteria mammaria, from the interior by means of a vessel separator.
Figure 7B:
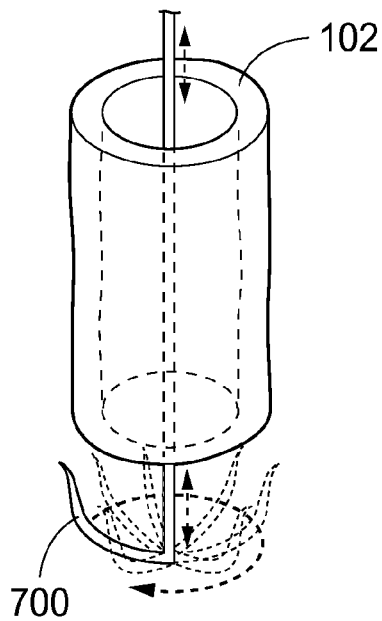
Figure 7C:
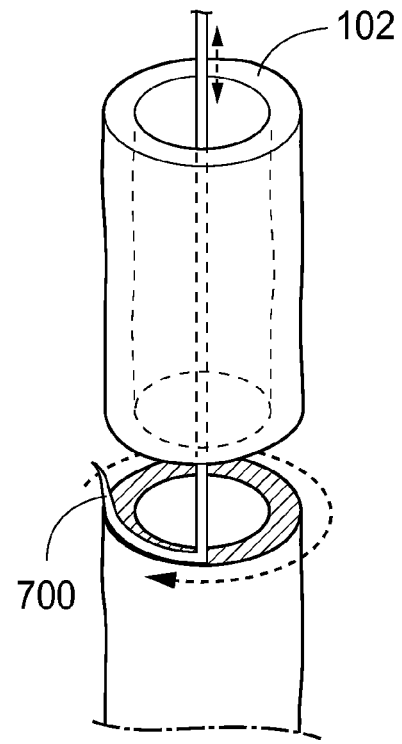
Figure 8:
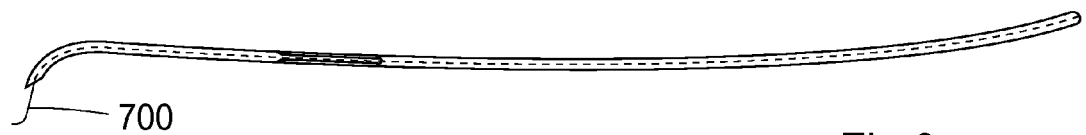
FIG. 8 is an illustration of a catheter that is finger-shaped on the distal tip, such as the port illustrated in FIG. 1B on the left, and a needle, such as the one illustrated in FIG. 1B on the right, guided therein.

As shown in FIGS. 7A, 7B, and 7C, the LIMA is mobilized with the aid of a finger-shaped catheter 700 on the tip, which dissects the LIMA from the thoracic wall and the surrounding tissue. The LIMA is accompanied by two veins along its extent. One of these veins, or both veins, can thus be used for task access to the place of mobilization after venous cannulization and catheterization. Consequently, the distal LIMA is liberated from its distal end blunt out of the thoracic wall over a sufficient length, approximately 3 cm for example, so that it can be anastomosized with a coronary vessel. It should be observed that the LIMA must be carefully liberated, as it otherwise can not fulfill its function after being damaged. This is illustrated in FIGS. 7A, 7B, and 7C, whereas this type of catheter is represented in FIG. 8. With the aid of the catheter, one may detach the LIMA on the exterior and thereby mobilize it over a specific length. This is done through a transluminal access, whereas in the simplest case, the instrument of mobilization is delivered on the basis of a catheter through the LIMA itself through to the place of mobilization.

Figure 9:
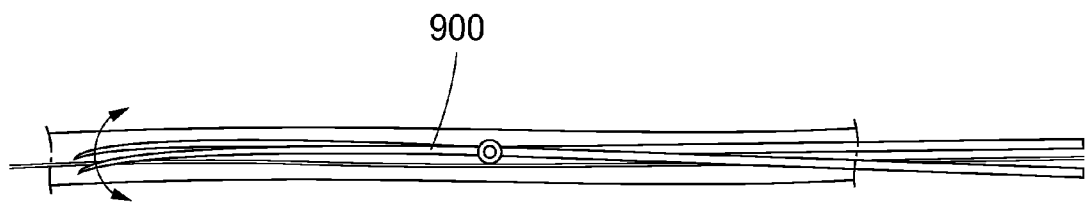
FIG. 9 is an illustration of a catheter forceps.

In doing so, the following instruments 900, having been supplied through a catheter, may be used among other things, small scissors, spreaders, or forceps, as illustrated in FIG. 9. In accordance with an embodiment of these instruments, in order to enable a function similar to instruments conventionally used by the surgeon, the tips of these spreaders are mounted using microtechnology to a catheter tip, and can thereby be used for preparation. Such catheter forceps are shown in FIG. 9.

Figure 10:
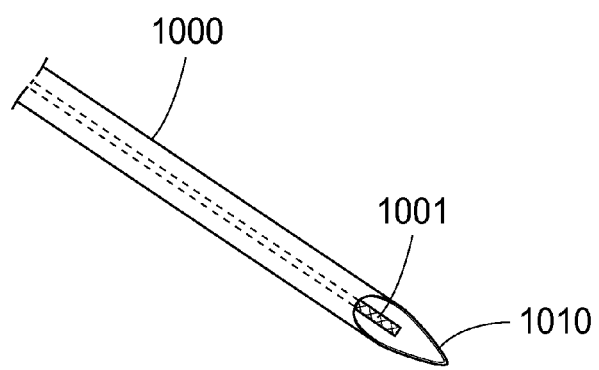
FIG. 10 is an illustration of a smart needle.

In FIG. 10, a "smart needle" is shown. A smart needle is a hollow needle with a Doppler crystal 1001 fixed on its tip 1010. Well-known embodiments of smart needles are conventionally used to make the pulsatile flow of the groin artery bearable in the groin of obese patients in order to find the correct place of cannulization. In the present process, one can also use the needles to find the coronary vessel from the vessel to be connected, for example the LAD starting from the LIMA.

A pressure wire, similar to the commercially available pressure wire of the company Radi Medical, may be used optionally within the framework of the present method. A pressure wire is a fine wire, which has routinely been used in coronary vessels with structures for pressure and flow registration before and behind the respective stenosis, in order to assess the significance of the stenosis. This is currently reimbursed by the health care funds in Germany in order to avoid unnecessary dilations of stent implantations. Within the framework of the present method, such a pressure wire may be used to give feedback over the situation of the catheter tip, to determine the penetration into a vessel or to assess the anastomosis carried out.

III. Occlusion of the Side Branches—Step 303:

The occlusion of the side branches occurs in step 303 of the process, for example with collagen or alcohol.

Referring to FIG. 1B, the LIMA may often be reached starting form the left arm through the previously inserted port 104. A catheter 160 bent to the side on the tip (such as an Amplatz catheter) may be inserted and brought forward with its tip into the side branch. By means of this catheter 160, diluted, toxic alcohol may be injected to close the small side branch. In the alternative, or in addition, collagen, thrombin, or other substances may be used.

The port tolerates multiple inflections, at least one by 90 degrees. The tip 180 is soft and the exterior shell may be provided with a clot-inhibiting coating (such as nitric oxide (NO)). In its middle, the port 3 has a mandrel which can be fed in and out flexibly and thereby causes a change in the rigidity, particularly in the middle section. The rigidity in the middle section allows the heart to change in its position and, like on a spoon, to lift a shorter distance in order to reach rear sections. The mandrel is hollow inside so that work can be performed, for example, insertion and extraction of instruments and wires. Important for the described method is the primary access through flexible ports which may be strengthened in the middle. It is thereby made possible to reach through to peripheral access to all places of the heart from outside through the thoracic cavity, whereby the heart may eventually be luxated.

As shown in FIG. 2, a balloon catheter 300 is used to close the side branches 200. By means of a balloon catheter, a drug is sprayed into the side branch of the LIMA, such as diluted alcohol, which closes the vessel. A balloon is arranged proximal to the distal opening, which is filled with contrast medium, in order to prevent the instilled drugs from draining out. Pain possibly experienced by the patient is treated beforehand with pain relievers.

However, step 303 may optionally be omitted as an occlusion of small side branches occurs through the body's own mechanisms. Practical results determine whether a closure of the side branches is necessary. In the age of minimally-invasive surgery, surgeons who were earlier of the opinion that all side branches had to be closed in order to achieve maximum blood flow towards the distal to the heart, hold today the view that this is not possible and is also no longer necessary because of the minimally-invasive access.

IV. Removal of the Distal LIMA—Step 304:

In step 304 of the method, the distal LIMA is removed by means of detachment and the closure of the distal LIMA. For example, this occurs with the aid of cryoablation or radio frequency (RF) ablation which is performed through the catheter.

This may be achieved in that the distal arterial mammaria and the side branches are detached blood tight with a "vessel separator" or "vessel cutter". An endoluminal detachment of vessels thereby occurs, which was previously not known. The detachment of vessels occurs with the aid of cauterization, cutting (bleeds) or electrocauterization (RF generator).

More precisely, this may be achieved in several ways, for example:
 1. through RF cauterization;
 2. through a cryo-catheter;
 3. through a small knife which cuts in a circular motion;
 4. by means of a metal stopper inserted through the port entry into the distal end of the LIMA with the aid of the catheter.

If energized, the metal stopper leads to a coagulation of the proximal opening of the distal portion of the vessel, which is no longer used and may also no longer lose any blood after this measure. The proximal LIMA portion cannot lose blood because the port inserted into the arm is built so conically towards the proximal end that it elastically closes the vessel (LIMA). Likewise, air does not get into the closed system as attention is paid to this during the procedure and the instruments used are designed correspondingly.

In this connection, RF current is introduced through the catheter proximally. In this manner, the distal ends in each case are "cooked", whereby they are closed. The proximal end of the detached LIMA remains open and is available for the further steps of the method.

Cryoablation, or more precisely in this case catheterablation with "cooling energy," represents an alternative to radio frequency (RF) energy. In cryoablation, cooling of the catheter tip to very low temperatures is performed. In doing so, a cryoprobe is inserted by the cardiologist endoluminal through the catheter. The catheter tip is cooled to temperatures between −70° C. and −80° C. in order to achieve the blood-tight effect.

During the distal anastomosis, the lungs are "held away" from the instrument through flat breathing. Alternatively, the left lung may be collapsed by means of a double lumen balloon tube and thereby kept away from the site of the operation. More precisely, selective ventilation of the lungs through the arrangement of a endotracheal tube with double lumen which work independently from one another for the intubation of the left and right main stem bronchial tubes.

Alternatively, from the start of the operation, the left lung is collapsed through the insertion of a basal lying thin catheter which causes a pneumothorax and may be used post-operatively for the evacuation of fluids (blood, contrast medium, etc.).

In most cases, it is sufficient during the procedure to ensure oxygenation through the right lung alone. With the aid of the double lumen tube, the left lung is temporarily not respirated under brief anesthesia. Alternatively, flat breathing is carried out. For critical patients a heart-lung machine (HLM) is possibly necessary.

If necessary, an endoluminal cauterization of the accompanying vein running alongside may take place. It is also conceivable that a hard wire is inserted into the accompanying vein or veins that carry with it a hollow cutting device to be developed or a "scraper", which detaches the LIMA in its distal 3 cm from the thoracic wall. It makes no difference whether the veins are damaged or not, as they ultimately are not needed.

With the aid of the catheter-based instrument, one may cauterize the LIMA on the outside and thus mobilize it over a specific length. This occurs through a transluminal access, wherein the mobilization instrument is delivered by means of a catheter through the LIMA itself to the mobilization site, in the simplest case. In this process, the inside of the LIMA may not be cauterized as the delicate LIMA can be harmed and would, consequently, no longer be suitable as a bypass vessel.

However, the distal LIMA itself is not harmed by the described method and will be used in the continued sequence of the method as an access way to the vessel to be bypassed.

Because the LIMA is now mobilized and detached, the catheter-based connection to a coronary vessel is still outstanding. This is described hereafter in step 305.

In difficult cases, the mobilization of the distal LIMA is possibly not necessary, whereas a direct puncture to the inside is possible in order to create an artificial anastomosis starting from that point, as described further below.

Figure 11:
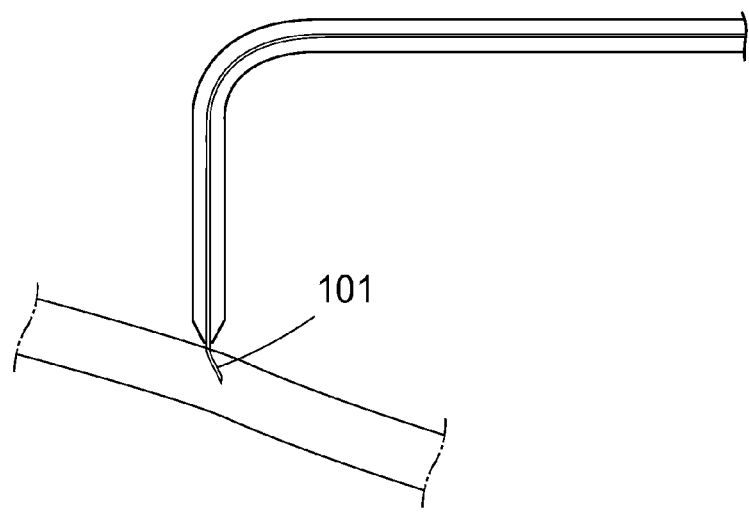
FIG. 11, an illustration of an access catheter with the smart needle introduced for puncturing a blood vessel, as in during EAS.
Figure 12:
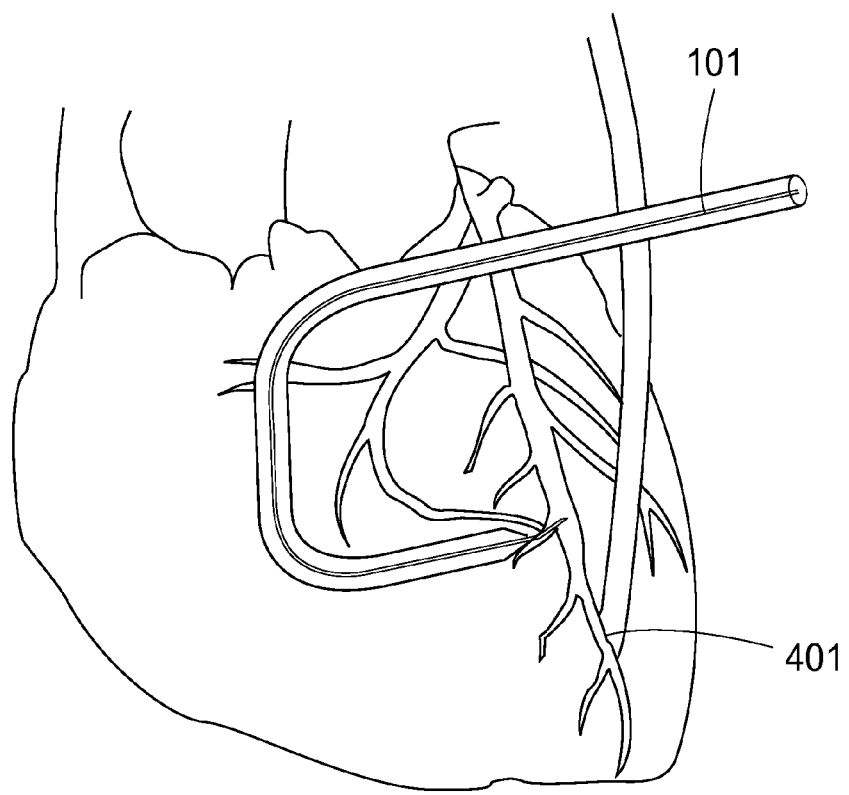
FIG. 12 is an illustration of a connection of the LIMA to the coronary vessel approximately in a 30-40 degree angle, and the catheter with the smart needle of FIG. 11 epicardially arranged for further bypass connections of coronary vessels.
Figure 13:
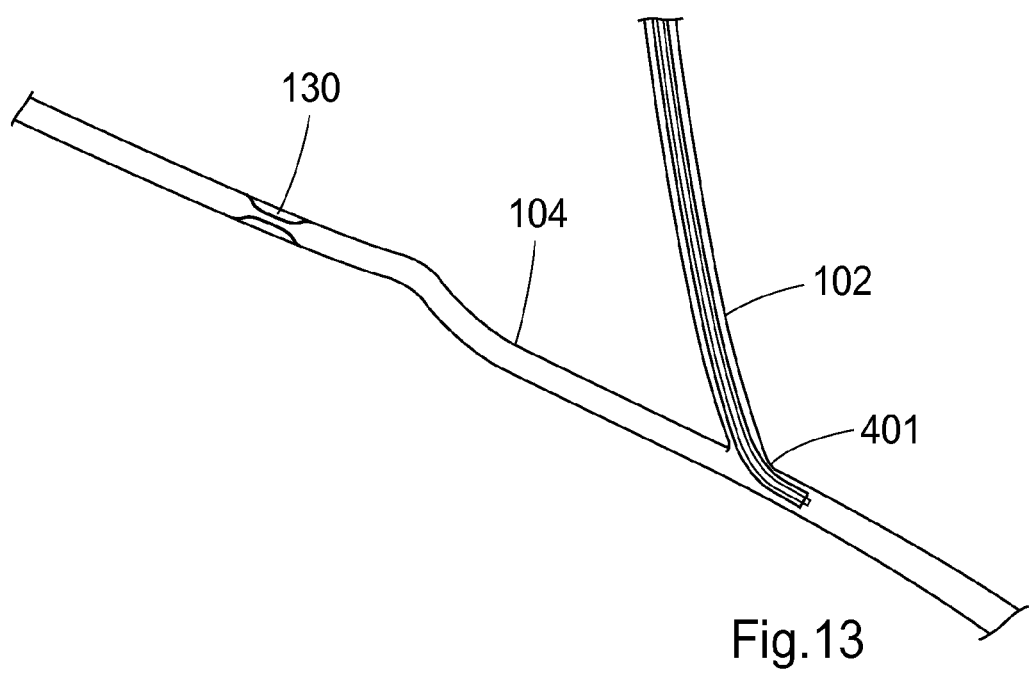
FIG. 13 is an illustration of an anastomosed bypass during EAS.

V. Cannulization of the Distal LAD—Step 305:

The probing of the LIMA occurs in step 305 of the method, for example with a fine Brockenborough, and the distal LAD is cannulized with a needle (see FIG. 11). The needle is present distally and is located on a material that is flexible but hard enough (such as a polymer similar to a Brockenborough catheter), that a sufficient "push" may be built up so that a puncture is made by the needle. Because the fore-area of the needle 103 is made of a relatively hard, but flexible polymer, a sufficient fastness is achieved in the longitudinal direction of the needle 103, whereupon it may be simultaneously maneuvered to the target cannulization area through passages with a tight radius of curvature. A needle assembly 3 is illustrated in FIG. 1B, comprising a handle 170 and various measuring scales for indicating the position of the tip at which the sharp needle 103 may be pushed out of the sheath 160 by pushing onto the proximal end 171 of the assembly 3.

The tip 180 of the port is soft so that it cannot do harm close to the moving heart. The tip 180 may thereby easily slide along the epicardium without harming the heart. It is important that the port tip is brought into the area of the anastomosis location through an interior, harder catheter that is controllable on the tip. For example, this is for anastomosis of the RCA on the posterior of the heart. For this purpose, this controllable catheter possibly also has a "paddle" on the tip or a broadening in order to charge the heart. The catheter and the port should be strengthened in the middle in order to manage the charging and mobilization of the heart.

The heart of an adult weighs approximately 300-500 grams. With the aid of a 5 cm long invasive implant behind the heart that is partially rigid on the end, movement of the heart may be achieved. It is possible through such a paddle movement to bring the heart, and consequently its coronary vessels, in a position favorable for the bypass connection.

The cannulization is normally made completely through the pericardium (heart sac which lies outside the heart). This is favorable for the hemodynamics, as the pericardium is necessary for this purpose. This is not the case for conventional heart surgery in which the heart sac must be opened wide and remains open after the operation.

The heart is examined and the coronary arteries are identified with the aid of imaging methods. The constricted or clogged coronary artery that will be provided with the bypass to be created may be identified visually and a suitable location may be selected distal or downstream from a blockage 130 for connection of the LIMA.

In addition to the needle, a "flattener" may also be inserted which minimizes the movement of the myocardium next to the coronary artery. The flattener may, for instance, have the form of a ski, runner, or fork. "Skis" enable a minimization of the heart wall movement in spite of a smaller mass. Even a ring flattener or octopus may be used. The flattener is inserted endoluminal with the needle and positioned. Alternatively, to the "skiers" equaling spacers to the heart which, in turn, equals local movement abater, a small suction cup may be attached to either move the heart somewhat as a whole or to minimize the movement locally, similar to in heart surgery, so that the needle may puncture the native coronary vessel.

From the left arm, the instruments move in direction of the heart by means of the vertically running LIMA. The LIMA is already detached through electrocauterization for example, and free in the thorax near to the LAD. The cannulization needle is delivered through the LIMA together with the harder fork ("skis"), which minimize the movement of the heart locally among themselves. That means that pressure is also exerted here from the outside. On the one hand, this allows the local minimization of movement of the beating heart and on the other hand allows the secure cannulization of the coronary vessel with the needle through stabilization with the fork of the flattener. Such a suction flattener may be used in the area of the rear and side wall.

An above-described pressure wire may be inserted through the cannulization needle to identify a coronary artery.

The entire measure takes place using imaging control, for example using X-ray control in the catheter laboratory, or endoscopic control.

VI. Creation of the LIMA-LAD Anastomosis—Step 306:

In step 306 of the method, a wire is inserted and the LIMA is connected with the coronary vessel with the aid of an anastomosis.

In respect to the control process, an angioscopy catheter, an ultrasound catheter, a thermography catheter, a tracking device, among other things, may be inserted to obtain the anastomosis or other necessary information. The pure X-ray control, which allows in part a three-dimensional depiction and has been used for decades as a standard diagnosis, is however sufficient to impart information concerning the situation to the cardiologist. This is how an angiography of the left ventricle occurs, for example, whereby a depiction of the LIMA starting from the left arm takes place in the same level. The three-dimensional representation allows the exact positioning of the cannulization needle. The localization of the anastomosis location is thus carried out by spraying the LAD (or the collateral vessel supplying the distal LAD) in conventional technology starting from the right groin, for example. The other groin serves as a place for cannulation for the potentially necessary emergency use of a heart-lung machine.

The mobilization of the heart may optionally occur through a cushion that may be filled with fluid which is inserted behind the heart. In doing so, the heart may be luxated forward in order to simplify the anastomosis from the front or in another desired position. The mobilization of the heart is consequently achieved through the corresponding positioning of the patient. The relocation of the heart may occur through a left side position in a special tray with gravity in the direction of the thoracic wall, so that the posterior wall is reached for an anastomosis on the right coronary artery (RCA) with a flexible catheter around the heart. If necessary, the heart may even be moved in the thorax and held with a hard, wide catheter tip.

Figure 15A:
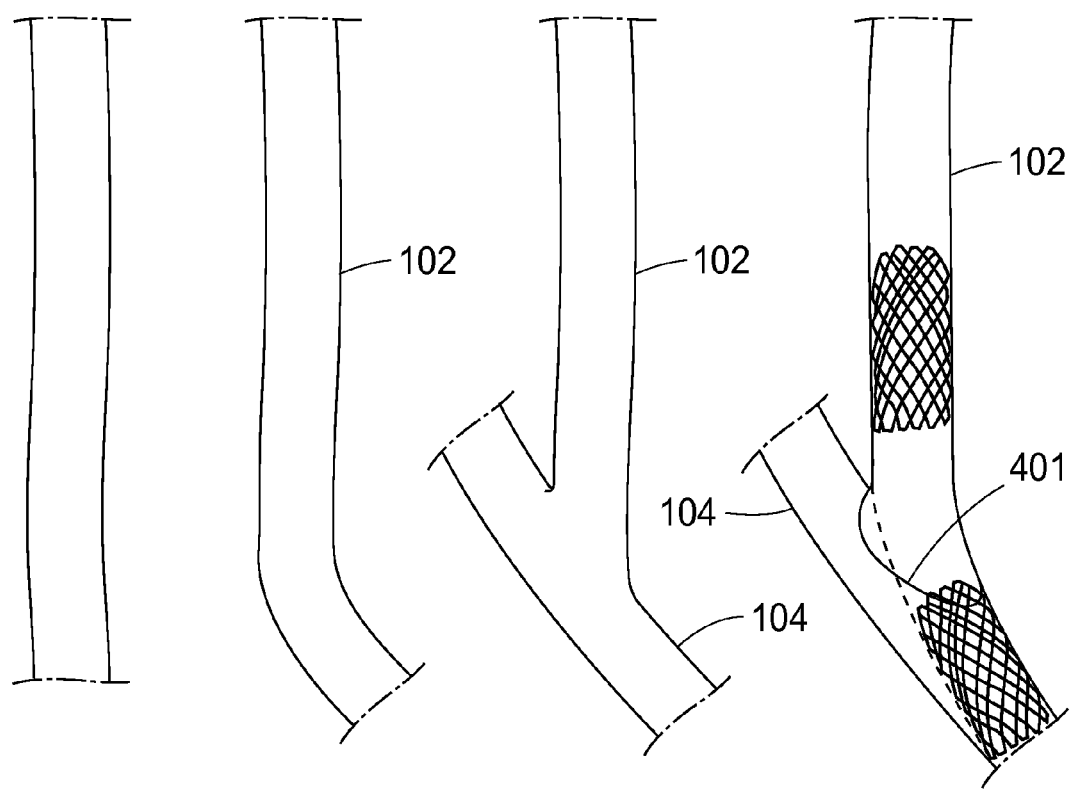
Figure 15B:
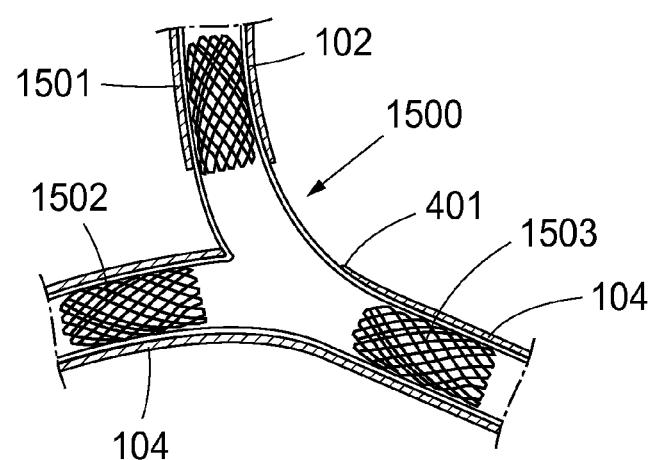
FIG. 15B is an illustration of vessel connection, wherein the connection is accomplished with the help of a bifurcation comprising stents for fixation of vessels.

The anastomosis of the LIMA to the coronary vessel occurs, for example, with one or more stents. Embodiments of such stents include a T-shaped or Y-shaped "three-arm" stent 1500, wherein the first arm is positioned in the LIMA 401 and each of the other arms 104, 102 lie in the coronary vessel, as shown in FIGS. 15A and 15B. The first arm (proximal) 1501 is covered in accordance with an embodiment, such as provided with a liquid-tight lining or coating. The lining or coating consists, for example, of a polymer material like PTFE or GoreTex®. Alternatively, the stent 1500 has a flexible distal part 1502 of the stent 1500 which enables flow towards the proximal, where the proximal stent portion is coated with drugs, if necessary. As depicted in FIG. 15B, the distal stent portion 1502 may be opened, if necessary, through a hinge or articulation. The proximal portion 1503 extends into the coronary artery and is covered. The rest is not covered and is coated with drugs, if necessary.

Figure 14A:
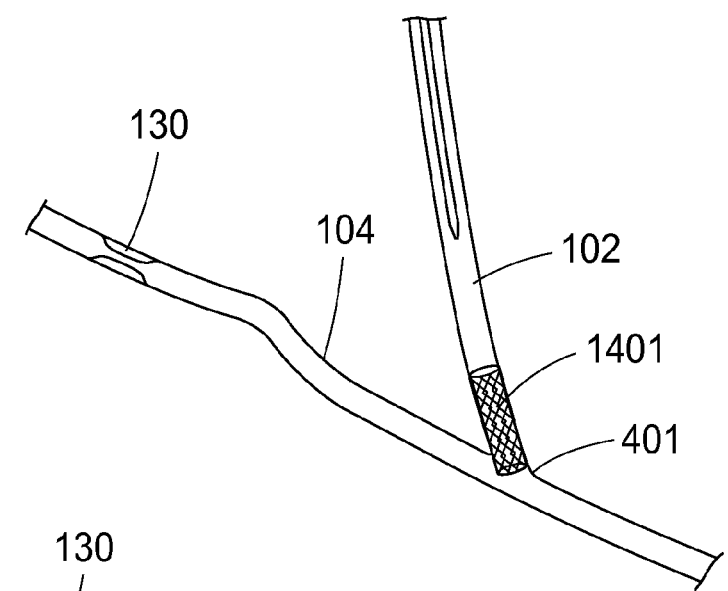
FIGS. 14A, 14B and 15A are illustrations of the insertion of a water-tight, covered stent for the anastomization of the LIMA to a coronary vessel.
Figure 14B:
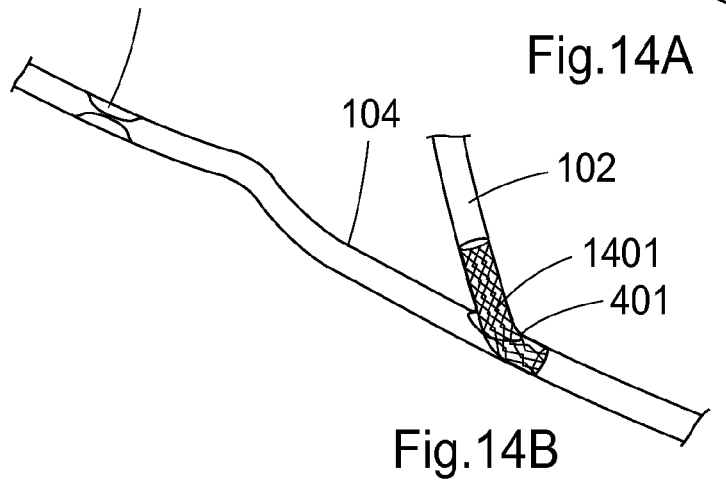

The connection to the coronary vessel occurs approximately at a 30°-40° angle, as well as with covered stents 1400 or partially covered stents 1401, see FIGS. 14A and 14B. The proximal PTFE coating of the stent, which guarantees blood tightness, is arranged so that this coating seals everything proximal up to the anastomosis (asymmetrical coating), but towards the distal is open and uncoated (or drug coated because, for the time being, no endothelialization takes place).

The stent may also be divided mechanically into two parts so that the distal, non-PTFE (or even PTFE coated) portion folds into the proximal LAD. The modeling of anastomoses by native vessels on the coronary tree is state of the art. It is new to do this after cannulization and to adduct blood through such measures from outside of the heart, because this anastomosis location may not be reached through proximal stenosis in the native vascular system.

An anastomosis may be improved with fibrin adhesives or tissue adhesives which are applied to the exterior of the stent.

Bifurcation stents may also be used, such as from Boston Scientific or Abbott. Such stents, however, have not been previously used for the vessel connections described herein. These stents are in each case also completely covered. FIG. 15B illustrates how the connection is effected with the aid of such a bifurcation stent. Within the stent, a magnet device may also be attached which forces the guide wire to go in a specific direction. A guide is also possible in this process which forces the wire to go in a specific direction, but this splint should be arranged so that the splint is not endothelialized.

The stent or the stents may also be connected through known bio-compatible vessel adhesive with the bypass vessels. The connection is made entirely without sutures. One possible vessel adhesive is fibrin adhesive, which has been successfully used in heart surgery for many years. However, due to its low adhesive strength it allows no independently adequate connection of tissues, but is unequalled as a hemostyptic agent due to its outstanding bio-compatibility. A different adhesive with good adhesive strength is the gelatin-resorcinol-glutar/formaldehyde glue, which creates a resilient, elastic tissue connection for application in the surgery of the dissection of the aorta. In addition, adhesives based on aldehyde are available. A commercially available adhesive is BioGlue® with an albumin and glutaraldehyde component which has high elasticity with good adhesive strength and low toxicity.

An anastomosis, such as a connection between two vessels, was performed conventionally by surgeons. However, it could also occur with the aid of a parallel shaped, beveled stent that is completely covered and has a swelling on the end of the stent with barbs. By simply pulling the stent backwards, it becomes fastened to the vessel wall. With the inflation of the stent, one then releases an acrylic adhesive to cement the stent. However, only on the outside, not in the lumen, which may not adhere. The end of the stent, for example, has a larger diameter over a length of approximately 1 mm because it extends into the vessel. Alternatively, the stent has a clip to hold the vessel open. The clip is inserted with a protective sheath and then pulled back. This type of ring-shaped clip, which is hollow on the inside, is used to connect the two vessels to one another. A vessel connection created in this manner is leak-proof directly after creation.

In doing so, the end of the stent is made visible in an X-ray image, such as with barium fiduciary markers. One consequently sees in the X-ray image exactly where the stent begins and ends. This is important to make the anastomosis leak-proof. With X-ray technology today, one achieves an accuracy of approximately 1/10 mm and practical performance is consequently possible. More markers are also possible in order to identify sections of the stent, wherein with a partially covered stent, the non-covered portion of the stent always goes into the coronary vessel.

The angle between the anastomosis vessel and the bypass vessel varies and this angle is often difficult to achieve, but this is enabled with controllable wires, for example, or with pre-fabricated stents with differing angles.

With the aid of the stent configuration, a vessel anastomosis is consequently prepared which enables a resistance-poor streamability for oxygen-rich blood transport, and thereby restores the blood supply of the heart muscle tissue to be supplied by the coronary artery. The stent remains in the body of the patient as a fastener, and also serves as a support and retention element after conclusion of the operative bypass procedure.

In conventional surgical procedures in OPCAB (off-pump coronary artery bypass) or MIDCAB (minimally invasive direct coronary artery bypass) procedures, the heart must be so strongly flattened, locally in its movement, so that the surgeon is able to perform his anastomosis suture. For a cannulization by means of a needle which has a lower mass, this is not necessary to this degree. A higher degree of local movement of the heart may be tolerated if the cannulization occurs quickly and systematically. The X-ray allows a high temporal resolution of the movement of the heart. It may be initially attempted to undertake a cannulization of the LAD without local flattening of the heart surface. A puncture completely through a vein is theoretically possible, but may be excluded through three-dimensional observation of the cannulization location or if necessary, through ultrasound examination or through venal angiography.

An erroneous puncture is certainly possible and may be immediately verified through contrast medium application in the internally hollow needle. Aborted cannulizations may not have any serious negative effects, according to prior detailed experimental experience of the applicant, as the vessel is cannulized in rather healthy areas and seals itself up again immediately.

After successful cannulization (verified by contrast medium application), a fine wire is brought forward in a conventional PTCA. It proceeds in the area of the distal LAD or other vessels to be anastomosed and adjusts itself to their course. This may be achieved through corresponding conventional angiography of the vessel, which represents the distal LAD. Up to now, the passage of the wire from the LIMA into the LAD is only dilated to the diameter of the cannulization needle. This location is traversed with a non-deployed balloon and is consequently widened ("dilated"). If necessary, it may also be dilated here. Blood will not leak out as the top of the port seals up. In the event that blood escapes in smaller amounts from the LAD or other vessels to be anastomosed, this may be tolerated. The actual anastomosis must then be quickly performed with the covered stent.

If the anastomosis with the covered stent is performed proximally in the area of the native LAD, where few or no vessels branch off, a perfusion of the proximal occluded LAD may possibly be done without.

Magnetic anastomoses may be used as an alternative to the stent vessel connection technology described. For example, metal rings may be attached to stents and pressed into the endothelium of vessels (dilated), so that a magnetic anastomosis may occur. Magnetic anastomosis devices are, for instance, disclosed in WO02/13703 to Cole, et al. or US2005/0080439 to Carson, et al., which are incorporated herein by reference in their entirety.

A careful "welding" of tissues may possibly be achieved through a slight change of temperature by means of a catheter probe. A conventional suture technique would be suitable, possibly based on microtechnology. For example, a suture may be accomplished through a disc found on the tip of the catheter in which a knurl with a mini-needle and rolled-up thread are found.

Further anastomoses may be created to further improve the blood supply of the coronary vessels, wherein the diagnosis of the respective patients is determined.

A bifurcation stent or a special stent (with proximal barbs) may be inserted laterally through cannulization of the arteria mammaria, which makes a junction possible. Additional vessels may then be anastomosed. Vessel management then occurs preferably directly below the bony thorax.

The special thing here is that the distal end of the LIMA is not used for the anastomosis, but are rather anastomoses or junctions artificially created laterally out of the LIMA which enable the diversion of the blood to a second or third vessel, similar to a so-called sequential bypass.

More precisely, this method comprises the following procedures:

(1) Cannulization of the LIMA laterally with a needle (see FIG. 16A);
(2) A wire is brought forward and through the internally hollow needle and the needle is pulled back;
(3) A catheter that is controllable on the tip is brought forward by means of the wire and into the area of a native coronary artery, such as the LAD, RCX or RCA;
(4) A GoreTex® implant pre-assembled on a balloon is brought forward by means of the catheter that is hollow in its interior, and placed on its tip in the area of a native coronary artery. The distal end is reinforced and provided with special self-expandable wires so that a seal to the LIMA occurs;
(5) A guide mandrel with a needle on the tip is brought forward by means of the GoreTex® implant that is hollow in the interior, so that the receiving native vessel (LAD, RCX, or RCA) may be cannulized. As an alternative to the GoreTex® implant, other implants or a native artery attached to a long balloon may also be used;
(6) The anastomosis of the GoreTex® vessel implant to the native vessel (LAD, RCX, or RCA) is performed with the aid of a stent connection.

Figure 17:
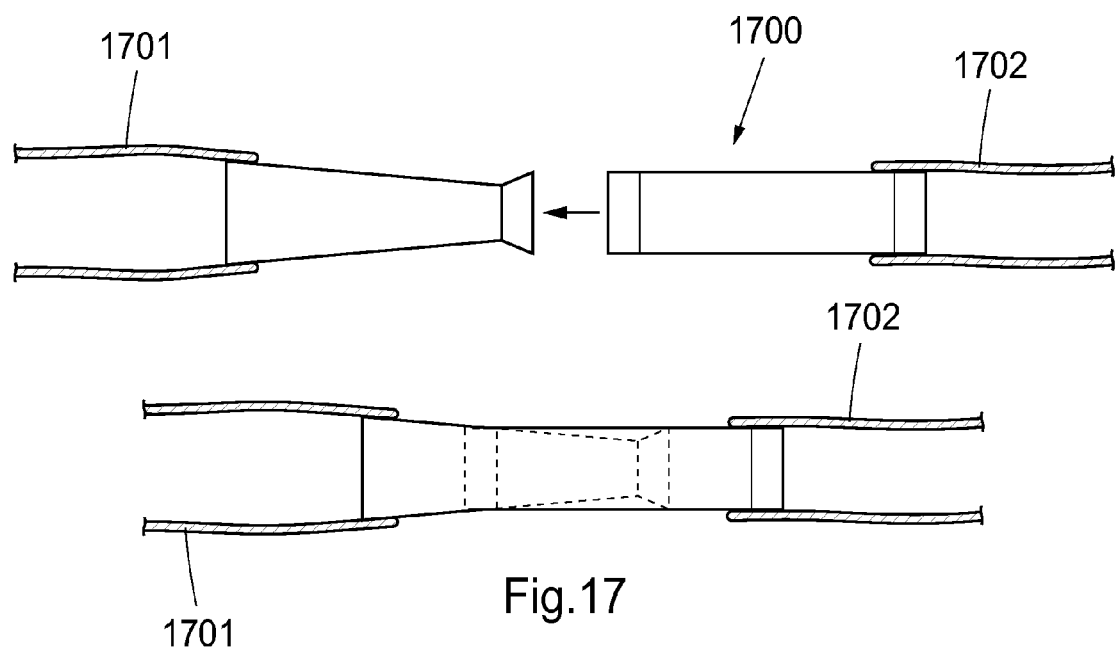
FIG. 17 is an illustration of instruments made of plastic or other materials which provide for a connection of blood vessels.

Instruments 1700 made of plastic or other materials may also be inserted which enable a type of click connection of vessels 1701, 1702, as illustrated in FIG. 17.

If necessary, the heart is mobilized with a suitable retainer and changed in its position. Retainer instruments may also be inserted by means of the LIMA or, should the space not be sufficient for this purpose with specific patients, a junction may be created directly from the subclavian artery by means of cannulization. However, this requires an arrest of the blood supply by means of a balloon in the area of the proximal subclavian artery.

At the connection of additional vessels via the free thoracic cavity, a wire is initially positioned and may be fastened through control from the outside. This deals with an almost exceedingly fine wire having almost no mass, wherein guide wires must be somewhat thicker than conventional (0.014 of an inch) to provide stability, but not too thick for the coronary vessel.

A flexible guide catheter with an atraumatic tip that is strongly reinforced on the tip in the middle (3-4 cm) may be used for the purpose of the heart being raised from the outside. The tip is atraumatic soft, whereas the middle is hard so that charging the heart is possible on the catheter ("surgical spoon"). This occurs in that the spoon is brought to the site through the LIMA when a wire is not sufficient for stabilization.

A NO (nitric oxide) releasing coating for the dilation of the vessel during the procedure may be applied to the instruments. The cannulization is then made in the area of the second vessel with a needle as described above, and the additional GoreTex graft is inserted and affixed. Such a procedure lasts only approximately 5 minutes for one junction with an additional vessel. Two to three vessels may thereby be connected within a half-hour.

Alternatively, the operation may also be performed under anesthetic control on fibrillating hearts. The heart may be slowed through a number of standard techniques, such as through electrical induction of a ventricular fibrillation.

Furthermore, alternatively or in addition, the subclavian artery may be cannulized and a "new vessel" anastomosized internally, such as a previously removed vein, a radial artery or a different artery, or a vessel graft made of GoreTex®, for example. In the connection of the right arteria mammaria interna (RIMA), the above-described methods and measures apply analogously.

Stents were previously used as opening devices for constricted vessels. Here they are used as connectors of two different vessels/vessel sections, for example of the LIMA to a coronary vessel. Because the inflow of blood should take place in the distal and in the proximal direction in the coronary vessel, the distal half of the stent may be normal, i.e. not covered, and the proximal portion of the stent may be covered, in order to guarantee leak tightness.

A GoreTex® implant may be attached to a long balloon/stent. Consequently, any number of vessel implants may be custom-made for the respective patients by the doctor working in the catheter laboratory. Previously removed veins or arteries may also be attached to such a balloon and connected with the vascular system with a stent in the proximal and distal area, see FIG. 3 and the description given above.

The stents are optimized for the special anastomosis implemented here. The form of the stent may be diamond-shaped, so that the lower edge extends further into the native vessel. A covering of the stent with PTFE or similar, is only partially present in the proximal area. The distal part of the stent is not covered and may be coated with drugs. The separation of both areas may be made visible through radio-opaque dots. As illustrated in FIG. 15B, a portion of the stent going left, may be brought into the proximal LAD without injury. However, it is not mandatory to use a bifurcation stent.

The portion of the stent cantilevered to the left, shown in FIG. 15B, is first opened at the location by an articulation in the stent bifurcation so that it protects the proximal native vessel in the area of commencement and secures the flow toward this point. It may be covered or not covered. It is so short, that it may be opened without harming the native vessel and the bifurcation.

Alternatively, a guide is arranged within the stent, as in a separate lumen for a wire, which directs it to the left or proximally into the native vessel.

A vessel junction may be created utilizing the present invention with the aid of stents. Firstly, in this method, a junction is completely created in an empty space with similar handgrips, and the implant is created from blood-tight vessel implants which are inserted by means of a balloon and then dilated. Blood is hereby introduced for the first time from outside by means of an external vessel.

Secondly, the anastomosis takes place in the healthy area, if anything.

Thirdly, the proximal area that is used here as an outlet area may not be reached without taking further steps due to the angle factors. However, this is solved through the present method.

This catheter or these catheters are finally removed from the body through the place of incision, which is surgically closed again through standard closure techniques. The possible anesthesia of the patient is ended and the procedure is concluded.

In addition to, or alternatively to, directly connecting the vessel as a shunt, as described in the previous section with reference to FIG. 6, a shunt graft vessel, as shown in FIG. 3, may be delivered by the above medical procedure. The step of removal of the vessel is then omitted and a connection is made by means of two anastomosis, namely one anastomosis in the access vessel (LIMA or RIMA) and one anastomosis in the vessel to which the blood flow from the access vessel is to be fluidly bypassed (LAD).

According to one embodiment, the instruments described may have a special atraumatic coating on the outside that possibly releases NO (nitric oxide), which has a vessel-protective and dilating effect, among other things.

Tissue adhesives may be mounted in a ring in the middle of the stent which accomplishes the fusion of the vessels and is only activated by a signal or measure from outside.

If required, a four-dimensional angiography image of the coronary artery tree may be made (angiography arcs travel around the patient). The corresponding cannulation point for the anastomosis is identified. The cannulation point may be precisely located through three-dimensional sensors, as used in electrophysiology, for example, or through other magnet-based localization systems in order to increase patient safety.

The method may be completely performed automatically by a robotic surgeon, namely robotically controlled with ECG and breathing synchronized.

With the aid of a novel contrast agent with longer retention time than previously, one may achieve the following.

The contrast agent remains bonded to the vessel wall for approximately 3-5 minutes. The entire vascular structure is collected in this time with coordinates and complete automation is possible. Erroneous punctures are excluded as millisecond-precise control takes place with reference to the heart activity. Renewed spraying with contrast agent is dispensed with in order to comprehend the vascular structure. This is gentler for the patients than previous procedures.

A phlebogram may be made in order to eliminate complications with cannulized veins.

ADVANTAGES

The above-described method and equipment exhibit, at least, the following advantages.

- Central vessels are not involved and there is no risk of damaging them or of causing complications through the procedure. As no intervention is undertaken on vital vessels or centrally supplying vessels, the overall risk of the intervention is substantially lower than previously. This may be accounted with the different ischemia period, the time in which irreversible damage is incurred by a body part otherwise supplied with blood during the absence of the blood supply. The ischemia period of the brain equals approximately 3 minutes, whereas the ischemia period of an extremity, like the arm, equals approximately 6 hours. If one damages a central vessel during a procedure, the patient or physician has 3 minutes at the most to take counter measures before irreparable brain damage occurs. In the present method, on the other hand, one has several hours available to undertake potential corrective emergency procedures. Therefore, the risk caused by the operation is substantially less.
- There is no clamping of the aorta and, therefore, no danger of a stroke exists, as explained earlier.
- No heart-lung machine is used, and therefore, no brain defects arise due to air bubbles in the heart-lung machine.
- A complete arterial revascularization is provideable.
- General anesthesia is not essential. The method is possible on persons who are fully awake.
- No cannulization of the heart is necessary. Cardioplegia may be dispensed with.
- Bypass operations are possible in hospitals without cardiac surgery. However, a heart-lung machine may be kept ready as security during a transition period.
- Potential post-operative treatment in an intensive care unit is substantially shortened.
- The epicardial access method has substantially lower complication prospects than conventional bypass procedures and the patient risk is substantially lower. In the worst case, complication prospects include the leakage of blood from the vessel into the left thorax. In this process, the vessel may be blocked at any time by means of the catheter or the port used in an emergency by means of a balloon mounted externally on the port. Furthermore, a pleural puncture may be made left or right at any time.

The monitoring or imaging feedback of the catheter position may be performed with the aid of a catheter laboratory, MRT (tied to a clinic or also outpatient) or ultrasound, as well. Therefore, an outpatient performance of the procedure is possible.

Significant time savings result as a consequence of the quick anastomosis, as compared to the conventional surgical technique.

Lower costs accrue for the method as the use of a heart-lung machine or general anesthesia are dispensed with.

There is indication that even patients are treatable that were previously excluded on the basis of concomitant disease due the lower cost for this type of bypass operation, such as patients with severe heart failure, severe lung disease, a tendency to bleed, kidney failure, stroke, or shock. Therefore, patients that were previously no longer accepted for surgery on the basis of concomitant disease may be treated.

Methods are possible for a wide group of patients as the method is less costly and has less risk for the patient.

It is not necessary to open the thoracic cavity.

The minimally-invasive bypass surgery is universally applicable for every patient and the result stands a comparison with the results of the well-known far more invasive bypass operations.

Non-invasive diagnosis and therapy is possible in every hospital without cardiac surgery where a heart-lung machine is in readiness.

The LIMA is mobilized or used as a point of origin. Dissection and separation are avoided. Several avenues are therefore possible over the course of the LIMA. If the LIMA is not sufficient, one may also use the RIMA.

GoreTex implants are reinforced so there is no adverse indications during.

The following aspects are significantly more advantageous than the previous procedures:
The procedure is significantly faster.
The procedure is significantly less expensive.
There are fewer risks to the patient.

What is claimed is:

1. A method of performing a minimally-intensive surgery of a coronary artery bypass on a patient, said method comprising:
creating a flow path from a body artery to a coronary artery with the aid of extracorporeal, catheter-based, endoluminal, minimally-invasive bypass surgery with feedback;
puncturing a left antecubital artery, thereby creating a left antecubital artery puncture;
bringing forward a sheath to reach a middle part of the left internal mammaria artery;
advancing a cardiac needle to reach the middle part of the left internal mammary artery; and
puncturing the left internal mammaria artery at said middle part to gain epicardial access, thereby creating a left internal mammaria artery punture.

2. The method according to claim 1, wherein said creating the flow path comprises creating of a direct path of flow from the body artery into the coronary artery.

3. The method according to claim 2, wherein said creating comprises connecting the body artery with the coronary artery by means of arranging a covered stent on the proximal side in the body artery.

4. The method according to claim 3, wherein said stent includes a mobile, distal stent-portion; the mobile, distal stent-portion enables flow towards the proximal side in the coronary artery.

5. A method of performing a minimally-intensive surgery of a coronary artery bypass on a patient, said method comprising:
creating a flow path from a left internal mammaria artery to a left anterior descending artery with the aid of extracorporeal, catheter-based, endoluminal, minimally-invasive bypass surgery with feedback;
wherein the creating of the flow path comprises the steps:
percutaneously probing the left internal mammaria artery starting from a portion of the body selected from the group consisting of the left arm and the left shoulder;
mobilizing the left internal mammaria artery with a catheter-based instrument;
closing of side branches of the left internal mammaria artery;
detaching the distal left internal mammaria artery;
probing of the left internal mammaria artery and puncturing the distal left anterior descending artery with a sharp instrument; and
connecting the left internal mammaria artery with the left anterior descending artery with the aid of an anastomosis;
wherein said method is performed without central anesthesia.

6. The method according to claim 5, wherein said puncturing is performed with a needle.

7. The method according to claim 5, further comprising controlling a puncture of the coronary vessel by using a trigger synchronized with the heart movement.

8. The method according to claim 5, wherein the method is performed robotically with ECG and breathing synchronized.

9. The method according to claim 5, wherein the feedback is an imaging feedback of the catheter position.

10. The method according to claim 9, wherein the imaging feedback occurs with the aid of a device selected from the group consisting of an X-ray modality, a magnetic resonance modality (MR), and an ultrasound modality.

11. The method according to claim 5, further comprising holding lungs of the patient at a distance from an anastomosis instrument by shallow breathing during a distal anastomosis of the body artery.

12. The method according to claim 5, further comprising artificially respirating the patient under anesthesia by ventilating a right and a left lung of the patient independently of one another via a double lumen balloon tube; collapsing and holding the left lung away from the site of the surgery.

13. The method according to claim 5, further comprising during the surgery, bringing a left lung of the patient into collapse through the insertion of a basal lying thin catheter, thereby causing a pneumothorax.

14. The method according to claim 13, further comprises evacuating fluids using a thin catheter post-operatively.

15. The method according to claim 1, further comprising using at least one medical device wherein said at least one medical device comprises:
a balloon catheter having an inflatable, expandable balloon centrally arranged at a distal end thereof;
a length of a blood tight tubular structure arranged coaxially around said balloon along a defined length at said distal end thereof;
at least one expandable fixation unit arranged coaxially between said tubular structure and said balloon wherein said fixation unit is arranged at an end of said tubular structure at least partly overlapping said end of said tubular structure;

at least one restriction unit arranged coaxially around said tubular structure; and a puncture needle; said using of said at least one medical device comprising crimping said fixation unit by said balloon to said ends of said tubular structure serving as a junction overlapping said coronary artery to be anastomosed.

16. The method according to claim 1, further comprising performing a medical cardiac bypass procedure through said left internal mammaria artery puncture.

17. The method according to claim 1, further comprising performing a procedure selected from the group consisting of a cardiac diagnostic, therapeutic, and further surgical procedure.

18. The method according to claim 17, wherein said procedure is an epicardial electrophysiology through said left internal mammaria artery puncture.

19. A method of performing a minimally-intensive surgery of a coronary artery bypass on a patient, said method comprising:

creating a flow path from a left internal mammaria artery to a left anterior descending artery with the aid of extracorporeal, catheter-based, endoluminal, minimally-invasive bypass surgery with feedback;

wherein the creating of the flow path comprises the steps:
percutaneously probing the left internal mammaria artery starting from a portion of the body selected from the group consisting of the left arm and the left shoulder;

mobilizing the left internal mammaria artery with a catheter-based instrument;

closing of side branches of the left internal mammaria artery;

detaching the distal left internal mammaria artery;

probing of the left internal mammaria artery and puncturing the distal left anterior descending artery with a sharp instrument;

connecting the left internal mammaria artery with the left anterior descending artery with the aid of an anastomosis; and building an artificial bifurcation from an artery selected from the group consisting of a right axillary artery, a left axillary artery, a right subclavian artery and a left subclavian artery to an internal mammary artery.

20. The method according to claim 5, further comprising an Epicardial Access Surgery providing at least one of diagnosis and therapy through catheterization with a closed thoracic wall, without the use of a heart-lung machine.

21. The method according to claim 5, wherein said method is performed in a catheterization laboratory as a routine procedure.

22. The method according to claim 5, comprising performing said method in a catheterization laboratory as a bail-out procedure when one of a conventional percutaneous endoluminal intervention has failed and a conventional percutaneous endoluminal intervention has led to a complication and the patient is in danger of death.

23. The method according to claim 5, wherein by performing said method results in very little blood leakage, thus avoiding blood supply and related blood donation procedures and risks.

24. The method according to claim 5, further comprising epicardially accessing of said coronary artery from said body artery for said bypass.

* * * * *